United States Patent
Guevremont et al.

(10) Patent No.: US 6,639,212 B1
(45) Date of Patent: Oct. 28, 2003

(54) METHOD FOR SEPARATION OF ISOMERS AND DIFFERENT CONFORMATIONS OF IONS IN GASEOUS PHASE

(75) Inventors: Roger Guevremont, Gloucester (CA); Randy Purves, Gloucester (CA); David Barnett, Orleans (CA)

(73) Assignee: National Research Council Canada, Ottawa (CA)

( * ) Notice: Subject to any disclaimer, the term of this patent is extended or adjusted under 35 U.S.C. 154(b) by 0 days.

(21) Appl. No.: 09/762,236

(22) PCT Filed: Aug. 5, 1999

(86) PCT No.: PCT/CA99/00714

§ 371 (c)(1),
(2), (4) Date: Apr. 12, 2001

(87) PCT Pub. No.: WO00/08454

PCT Pub. Date: Feb. 17, 2000

Related U.S. Application Data

(63) Continuation of application No. 09/321,820, filed on May 28, 1999, now Pat. No. 6,504,149.
(60) Provisional application No. 60/095,481, filed on Aug. 5, 1998.

(30) Foreign Application Priority Data

Jan. 29, 1999 (CA) .............................................. 2260572

(51) Int. Cl.⁷ ................................................ H01J 49/40
(52) U.S. Cl. ...................................... 250/282; 250/281
(58) Field of Search .............................. 250/282, 281, 250/283, 286, 292, 290, 293

(56) References Cited

U.S. PATENT DOCUMENTS

| 3,668,383 | A | 6/1972 | Carroll |
|---|---|---|---|
| 4,855,595 | A | 8/1989 | Blanchard |
| 5,420,424 | A | 5/1995 | Carnahan et al. |
| 5,723,861 | A | 3/1998 | Carnahan et al. |
| 5,736,739 | A | 4/1998 | Uber et al. |
| 5,789,745 | A | 8/1998 | Martin et al. |
| 5,801,379 | A | 9/1998 | Kouznetsov |
| 5,869,831 | A | 2/1999 | De La Mora et al. |
| 5,905,258 | A | 5/1999 | Clemmer et al. |
| 6,041,734 | A | 3/2000 | Raoux et al. |
| 6,162,709 | A | 12/2000 | Raoux et al. |
| 6,323,482 | B1 | 11/2001 | Clemmer et al. |
| 6,504,149 | B2 * | 1/2003 | Guevremont et al. ....... 250/286 |

FOREIGN PATENT DOCUMENTS

| WO | WO00/63949 | 10/2000 |
|---|---|---|
| WO | WO01/22049 A2 | 3/2001 |

OTHER PUBLICATIONS

Buryakov, I.A., Krylov, E. V., Nazarov, E. G., and Rasulev, U. K., A new method of separation of multi–atomic ions by mobility at atmospheric pressure using a high–frequency amplitude–asymmetric strong electric field, Int. J. Mass Spectrom. Ion Processes, 128, 143 (1993).

(List continued on next page.)

Primary Examiner—Kiet T. Nguyen
(74) Attorney, Agent, or Firm—Freedman & Associates

(57) ABSTRACT

The present invention relates to a method of separating ions having the same mass to charge ratio but different ion mobility characteristics, based on the ion focussing principles of high field asymmetric waveform ion mobility spectrometry. Isomers including gas-phase molecular anions of the amino acids leucine and isoleucine are separable by the method of the present invention. Identification of different conformers of ions at the same charge state, including conformers present at certain charge states of the protein bovine ubiquitin, is also possible using the method of the present invention.

57 Claims, 26 Drawing Sheets

OTHER PUBLICATIONS

Krylov, E. V., A method of reducing diffusion losses in a drift spectrometer, Tech. Phys., 44, 113 (1999).

Carnahan, B., Day, S., Kouznetsov, V., Matyjaszcyk, M., and Tarassov, A.,Field Ion Spectrometry—A New Analytical Technology for Trace Gas Analysis, Proceedings of the 41st Annual ISA Analysis Division Symposium, , Framingham, MA, pp. 85 (1996).

Riegner, D. E., Harden, C. S., Carnahan, B., and Day, S., Qualitative Evaluation of Field Ion Spectrometry for Chemical Warfare Agent Detection, Proceedings of the 45th ASMS Conference on Mass Spectrometry and Allied Topics, , Palm Springs, California, pp. 473 (1997).

Spangler, G. E., Fundamental considerations for the application of miniature ion mobility spectrometry to field analytical applications, Field Analytical Chemistry and Technology, 4, 255 (2000).

Eiceman, G. A., Nazarov, E. G., Tadjikov, B., and Miller, R. A., Monitoring volatile organic compounds in ambient air inside and outside buildings with the use of a radio–frequency–based ion–mobility analyzer with a micromachined drift tube, Field Anal. Chem. Tech., 4, 297 (2000).

Miller, R. A., Nazarov, E. G., Eiceman, G. A., and King, A. T., A MEMS radio–frequency ion mobility spectrometer for chemical vapor detection, Sensors and Actuators A, 91, 307 (2001).

Eiceman, G. A., Tadjikov, B., Krylov, E., Nazarov, E. G., Miller, R. A., Westbrook, J., and Funk, P., Miniature radio–f-requency mobility analyzer as a gas chromatographic detector for oxygen–containing volatile organic compounds, pheromones and other insect attractants, J. Chromatogr. A, 917, 205 (2001).

Miller, R. A., Eiceman, G. A., Nazarov, E. G., and King, A. T., A novel micromachined high–field asymmetric waveform–ion mobility spectrometer, Sensors Actuators B Chem, 67, 300 (2000).

Hudgins, R. R., Woenckhaus, J., and Jarrold, M. F., High resolution ion mobility measurements for gas phase proteins: correlation between solution phase and gas phase conformations, Int. J. Mass Spectrom, Ion Processes, 165/166, 497 (1997).

Collings, B. A., and Douglas, D. J., Conformation of gas–phase myoglobin ions, J. Am. Chem. Soc., 118, 4488 (1996).

Covey, T., and Douglas, D. J., Collision cross sections for protein ions, J. Am. Soc. Mass Spectrom., 4, 616 (1993).

Cox, K. A., Julian Jr., R. K., Cooks, R. G., and Kaiser Jr., R. E., Conformer selection of protein ions by ion mobility in a triple quadrupole mass spectrometer, J. Am. Soc. Mass Spectrom., 5, 127 (1994).

Spangler, G. E., and Miller, R. A., Application of mobility theory to the interpretation of data generated by linear and RF excited ion mobility spectrometers, Int. J. Mass Spectrom., 214, 95–104 (2002).

Kiai, S. M. S., Confinement of ions in a radio frequency quadrople ion trap supplied with a periodic impulsional potential, Int. J. Mass Spectrom., 188, 177 (1999).

Kiai, S. M. S., Andre, J., Zerega, Y., Brincourt, G., and Catella, R., Study of a Quadrupole Ion Trap Supplied with a Periodic Implusional Potential, Int. J Mass Spectrom. and Ion Processes, 107, 191 (1991).

Whetten, N. R., Macroscopic particle motion in quadrupole fields, J. Vac. Sci. Technol., 11, 515 (1974).

Buryakov, I. A., Kolomiets, Y.N., and Luppu, B. V., Detection of Explosive Vapors in the Air Using an Ion Drift Nonlinearity Spectrometer, J. Anal. Chem., 56, 336 (2001).

Krylov, E. V., Pulses of Special Shapes Formed on a Capacitive Load, Instruments and Experimental Techniques, 40, 628 (1997).

\* cited by examiner

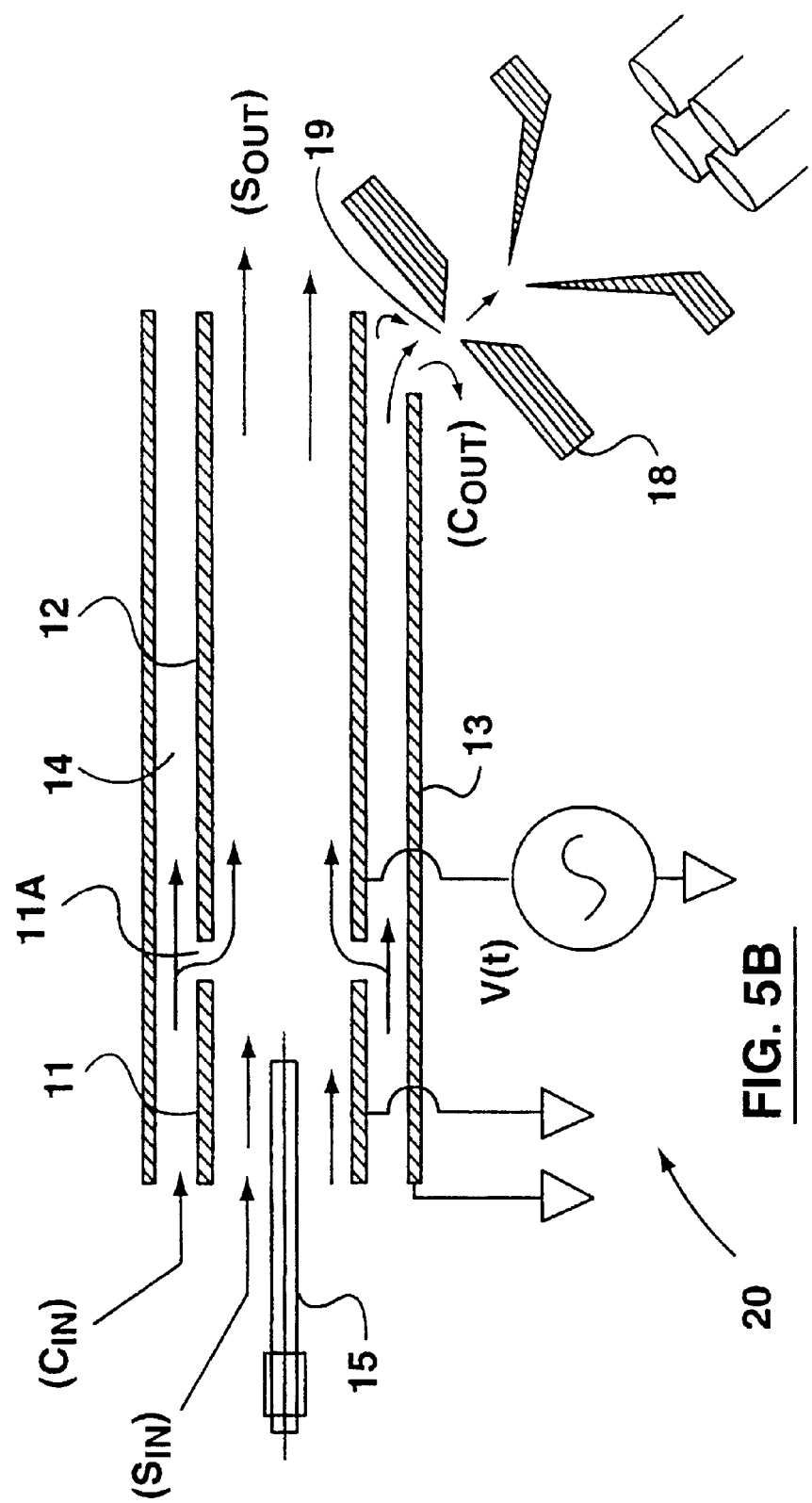

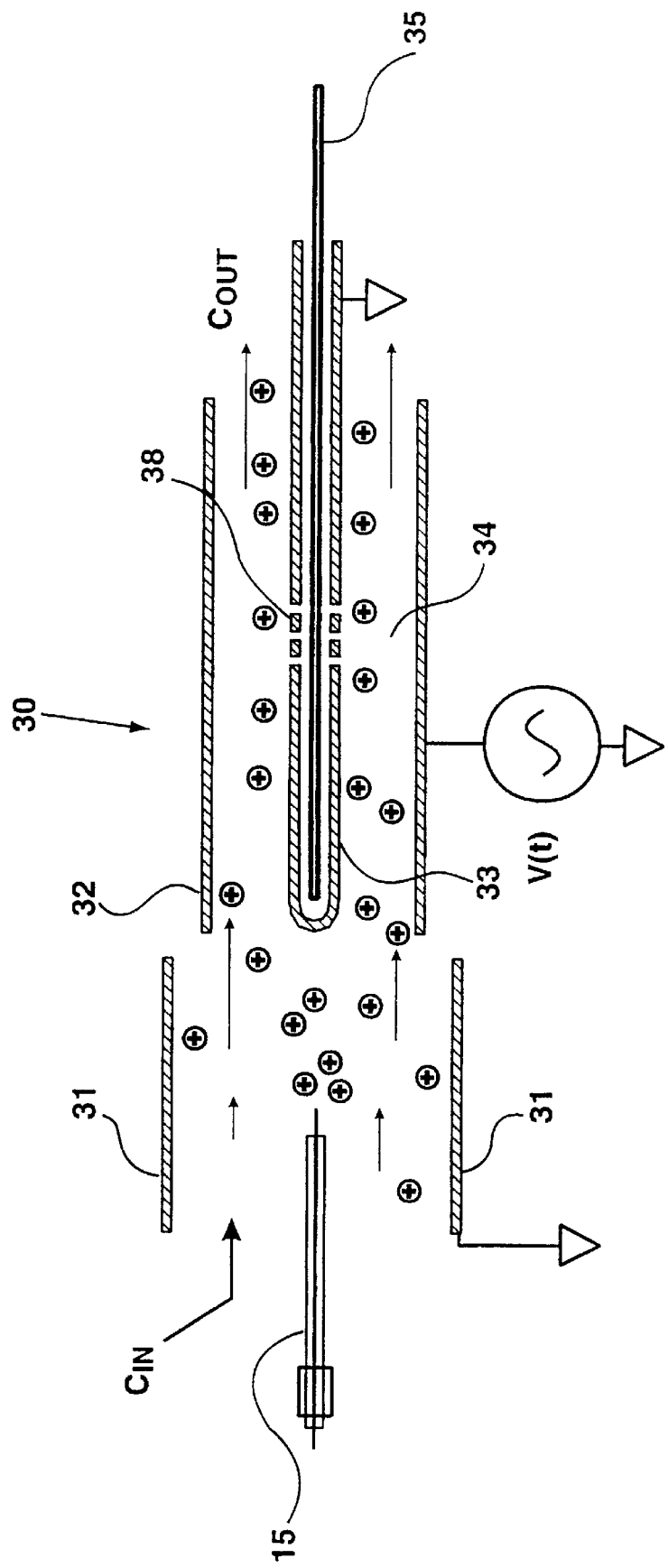

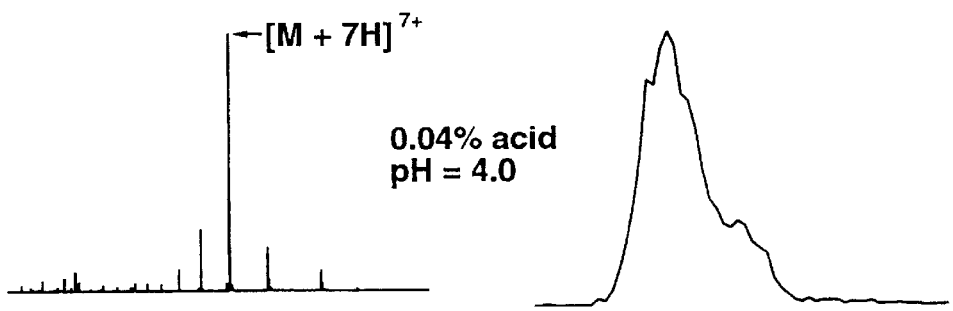
FIG. 16A  FIG. 16B
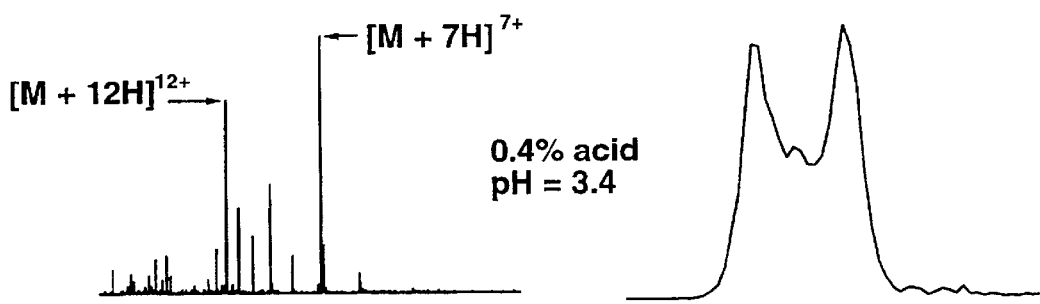
FIG. 16C  FIG. 16D
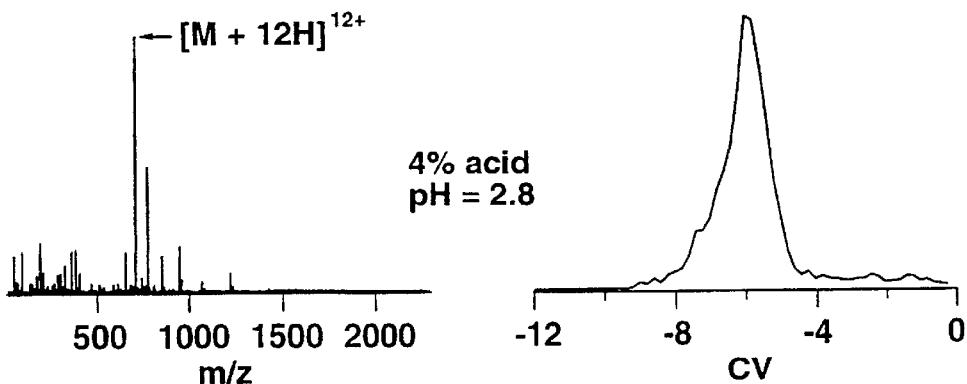
FIG. 16E  FIG. 16F charge state = +7        charge state = +8        charge state = +9

(I) 0.04% acid  
pH = 4.0

(II) 0.4% acid  
pH = 3.4

(III) 4% acid  
pH = 2.8

| | charge state = +7 | charge state = +8 | charge state = +9 |
|---|---|---|---|
| pH = 2.8 | 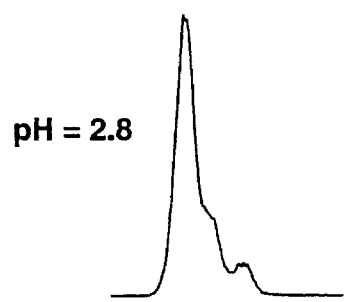<br>FIG. 18A | 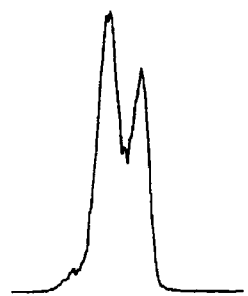<br>FIG. 18B | 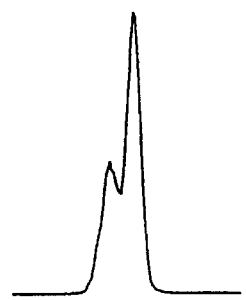<br>FIG. 18C |
| pH = 2.1 | 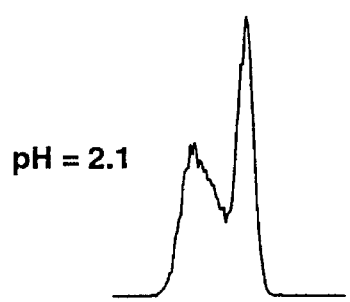<br>FIG. 18D | 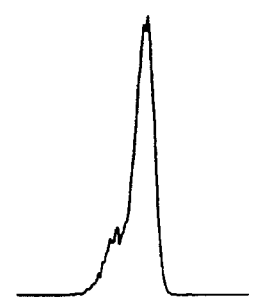<br>FIG. 18E | 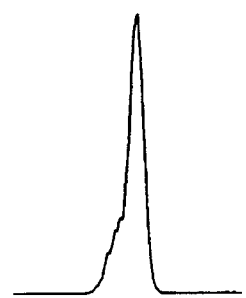<br>FIG. 18F |
| pH = 1.8 | 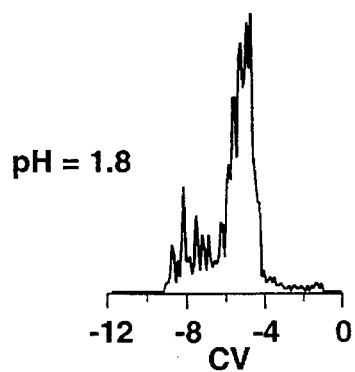<br>FIG. 18G | 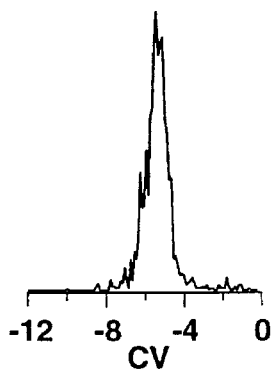<br>FIG. 18H | 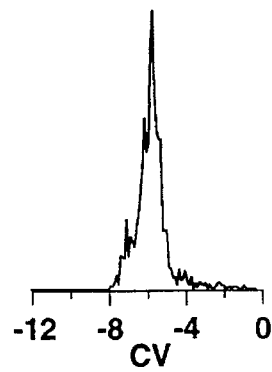<br>FIG. 18I |

50 % methanol mass spectra

45 % methanol

TIC

+8

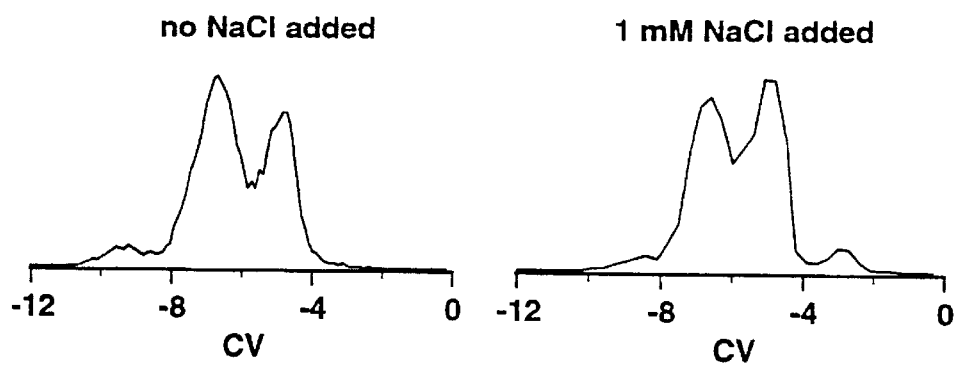
FIG. 21A (no NaCl added)  FIG. 21B (1 mM NaCl added)
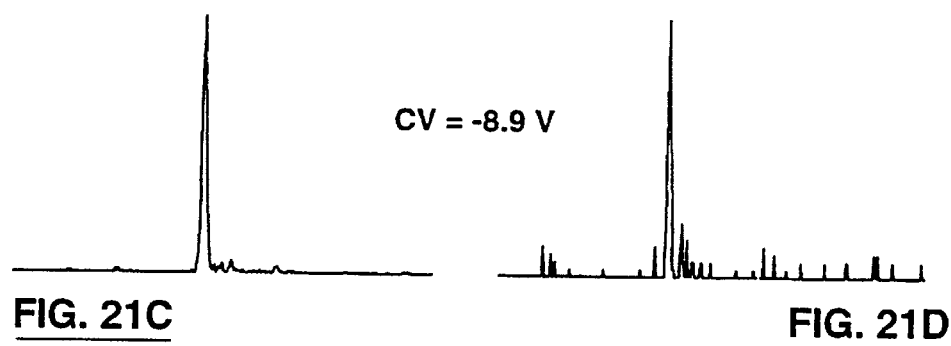
CV = -8.9 V
FIG. 21C  FIG. 21D
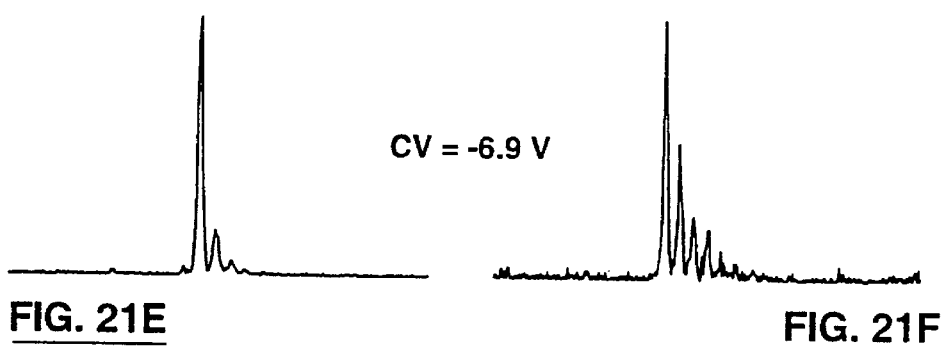
CV = -6.9 V
FIG. 21E  FIG. 21F
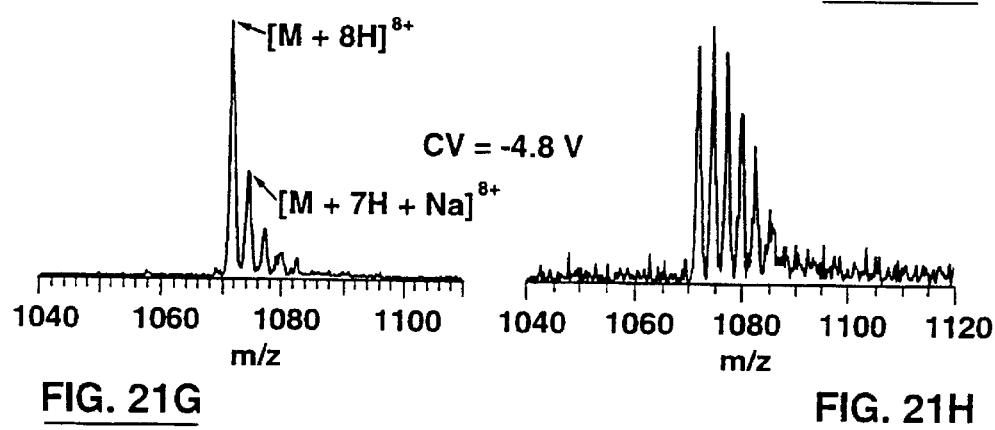
$[M + 8H]^{8+}$
$[M + 7H + Na]^{8+}$
CV = -4.8 V
FIG. 21G  FIG. 21H

METHOD FOR SEPARATION OF ISOMERS AND DIFFERENT CONFORMATIONS OF IONS IN GASEOUS PHASE

This application is a continuation of U.S. patent application Ser. No. 09/321,820 filed May 28, 1999 now issued as U.S. Pat. No. 6,504,149 on Jan. 7, 2003, which is a 371 of International Application No. PCT/CA99/00714 filed Aug. 5, 1999, which claims the benefit of U.S. Provisional Application No. 60/095,481 filed Aug. 5, 1998.

FIELD OF THE INVENTION

The present invention relates to a method for separating isomers and different conformations of ions in gaseous phase, based on the principle of high field asymmetric waveform ion mobility spectrometry.

BACKGROUND OF THE INVENTION

High sensitivity and amenability to miniaturization for field-portable applications have helped to make ion mobility spectrometry an important technique for the detection of many compounds, including narcotics, explosives, and chemical warfare agents (see, for example, G. Eiceman and Z. Karpas, *Ion Mobility Spectrometry* (CRC. Boca Raton, Fla. 1994); and Plasma Chromatography, edited by T. W. Carr (Plenum, New York, 1984)). In ion mobility spectrometry, gas-phase ion mobilities are determined using a drift tube with a constant electric field. Ions are gated into the drift tube and are subsequently separated based upon differences in their drift velocity. The ion drift velocity is proportional to the electric field strength at low electric fields (e.g., 200 V/cm) and the mobility, K, which is determined from experimentation, is independent of the applied field. At high electric fields (e.g. 5000 or 10000 V/cm), the ion drift velocity may no longer be directly proportional to the applied field, and K becomes dependent upon the applied electric field (see G. Eiceman and Z. Karpas, *Ion Mobility Spectrometry* (CRC. Boca Raton, Fla. 1994); and E. A. Mason and E. W. McDaniel, *Transport Properties of Ions in Gases* (Wiley, New York, 1988)). At high electric fields, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry (see I. Buryakov, E. Krylov, E. Nazarov, and U. Rasulev, Int. J. Mass Spectrom. Ion Proc. 128. 143 (1993); D. Riegner, C. Harden, B. Carnahan, and S. Day, Proceedings of the 45th ASMS Conference on Mass Spectrometry and Allied Topics, Palm Springs, Calif., Jun. 1–5, 1997, p. 473; B. Carnahan, S. Day, V. Kouznetsov, M. Matyjaszczyk, and A. Tarassov, Proceedings of the 41st ISA Analysis Division Symposium, Framingham, Mass., Apr. 21–24, 1996, p. 85; and B. Carnahan and A. Tarassov, U.S. Pat. No. 5,420,424). Ions are separated in FAIMS on the basis of the difference in the mobility of an ion at high field $K_h$ relative to its mobility at low field K. That is, the ions are separated because of the compound dependent behaviour of $K_h$ as a function of the electric field. This offers a new tool for atmospheric pressure gas-phase ion studies since it is the change in ion mobility and not the absolute ion mobility that is being monitored.

An instrument based on the FAIMS concept has been designed and built by Mine Safety Appliances Company of Pittsburgh, Pa. ("MSA") for use in trace gas analysis. The MSA instrument is described in U.S. Pat. No. 5,420,424 and is available under the trade mark FIS (for Field Ion Spectrometer). While the use of the MSA instrument (and similar instruments based on the FAIMS concept) for trace gas analysis is known, the inventors believe that they have identified certain heretofore unrealized properties of these instruments which make them more versatile. Based on this realization, the inventors have developed what is believed to be a previously unknown method for separation of isomers and different conformations of ions. A summary and detailed description of the present invention is provided below.

SUMMARY OF THE INVENTION

The present invention provides a method for identifying ions having substantially the same mass to charge ratio but having different ion mobility characteristics, comprising the steps of:

a) providing at least one ionization source of ions;

b) providing an analyzer region defined by a space between at least first and second spaced apart electrodes, said analyzer region being in communication with a gas inlet, a gas outlet, an ion inlet and an ion outlet, and introducing said ions into said analyzer region through said ion inlet;

c) applying an asymmetric waveform voltage and a direct current compensation voltage to at least one of said electrodes;

d) setting said asymmetric waveform voltage;

e) varying said direct current compensation voltage and measuring resulting transmitted ions at said ion outlet, so as to produce a compensation voltage scan for said transmitted ions; and f) identifying peaks in said compensation voltage scan.

The method may further comprise the step of setting said direct current compensation voltage to correspond to one of said peaks to separate a desired ion from other ions with substantially the same mass to charge ratio.

Advantageously, the above method is operable at substantially at atmospheric pressure and substantially at room temperature.

The method may further include detecting said transmitted ions by mass spectrometry.

Typically, the method includes providing a gas flow through said analyzer region, so as to transport said ions along said analyzer region, although it will be understood that other ion transport means are possible.

Furthermore, in identifying a peak, it will be understood that the term peak is not limited to the apex of the peak, and that a peak will typically have a noticeable width, or a compensation voltage range in which the peak appears.

BRIEF DESCRIPTION OF THE DRAWINGS

For a better understanding of the present invention, and by way of example, reference will now be made to the accompanying drawings, which show preferred embodiments of the present invention in which:

FIGS. 5A and 5B show schematically the coupling of the FAIMS apparatus of FIGS. 3A and 3B together with a mass spectrometer;

FIGS. 6A and 6B shows schematically a FAIMS apparatus for measuring the ion distribution in the analyzer region;

FIG. 10 trace (b) shows an IS-CV spectrum of a leucine/isoleucine mixture;

FIGS. 16A, 16C, and 16E show mass spectra showing the effect of the amount of acetic acid on ESI mass spectra of a solution of bovine ubiquitin;

FIGS. 16B, 16D, and 16F show TIC-CV spectra corresponding to the ESI-mass spectra obtained in FIGS. 16A, 16C, and 16E, respectively;

FIGS. 18A–18I show IS-CV spectra showing the effect of the amount of HCl in a solution of bovine ubiquitin on the charge states +7, +8 and +9;

FIGS. 21A and 21B show the effect of adding NaCl to a solution of bovine ubiquitin on the IS-CV spectrum for charge state +8;

FIGS. 21C through 21H show mass spectra of different CV values;

DETAILED DESCRIPTION OF THE INVENTION

As an important preliminary note, the discussion below generally uses the term "ion" to mean a charged atomic or molecular entity, the "ion" can be any electrically charged particle, solid or liquid, of any size. The discussion below refers to both positively charged and negatively charged ions, and it will be understood by a person skilled in the art that, for any individual analysis, only one of these types of ions will be used.

The discussion below also uses the term "isomers" to mean compounds having identical molecular formulas but which differ in the ways in which the atoms are bonded to each other. Generally speaking, isomers may be constitutional isomers or stereoisomers. Constitutional isomers differ in the order and the way in which atoms are bonded together in their molecules. Stereoisomers differ only in the arrangement of their atoms in space. Stereoisomers that are nonsuperimposable mirror images of each other are called enantiomers. Stereoisomers that are not enantiomers are called diastereomers. Also, the lack of free rotation around carbon-carbon bonds may form cis-trans isomers where two substituents may be on opposite sides of a plane (trans) or on the same side of a place (cis). Finally, positional isomers (e.g. ortho, meta, and para positions within a carbon ring) and geometrical isomers may form in various types of compounds.

The disclosure also uses the term "ion selected compensation voltage" (IS-CV) spectra which refers to scanning the compensation voltage applied to a FAIMS analyzer, as discussed below, typically while monitoring a single mass-to-charge (m/z) value. The term "total ion current compensation voltage" (TIC-CV) spectra is also used to refer to a compensation voltage scan which shows the sum of a signal for all detected ions in a given m/z range.

Principles of FAIMS

The principles of operation of FAIMS have been described in Buryakov et. al. (see I. Buryakov, E. Krylov, E. Nazarov, and U. Rasulev, Int. J. Mass Spectrom. Ion Proc. 128. 143 (1993)) and are summarized here briefly. The mobility of a given ion under the influence of an electric field can be expressed by: $K_h(E)=K(1+f(E))$, where $K_h$ is the mobility of an ion at high field, K is the coefficient of ion mobility at low electric field and "f(E)" describes the functional dependence of the ion mobility on the electric field (see E. A. Mason and E. W. McDaniel, *Transport Properties of Ions in Gases* (Wiley, New York, 1988); and I. Buryakov, E. Krylov, E. Nazarov, and U. Rasulev, Int. J. Mass Spectrom. Ion Proc. 128. 143 (1993)).

Figure 1:
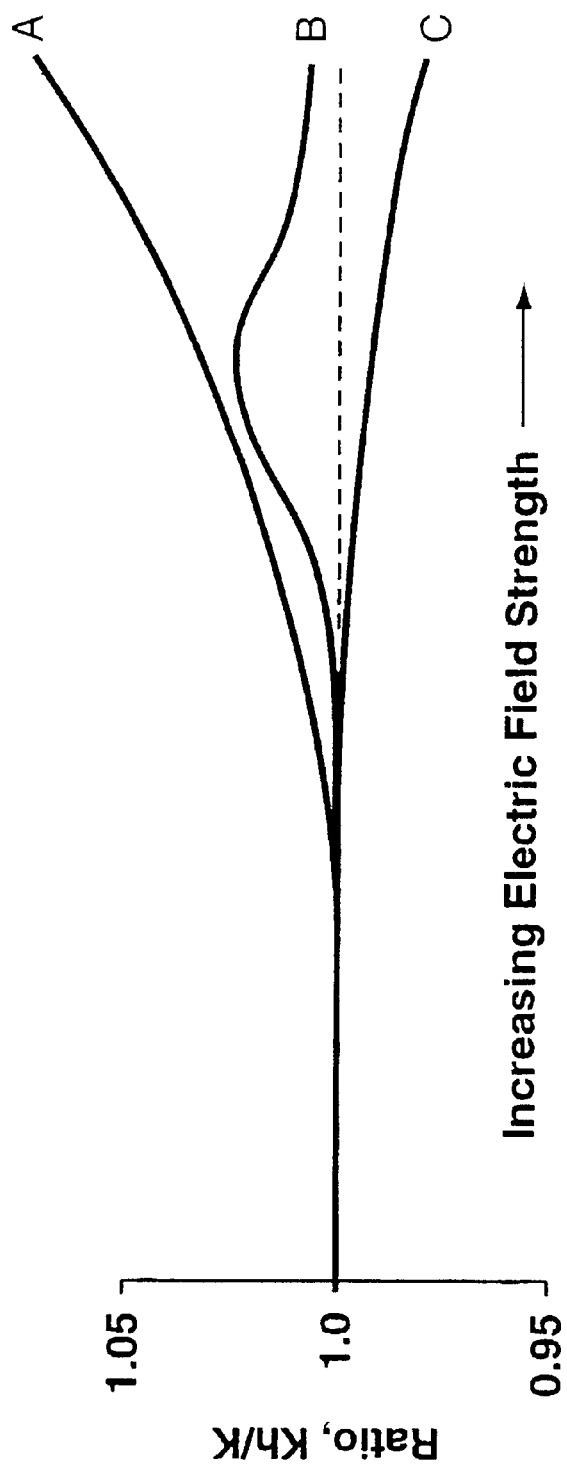
FIG. 1 shows three possible examples of changes in ion mobility as a function of the strength of an electric field.
Figure 2:
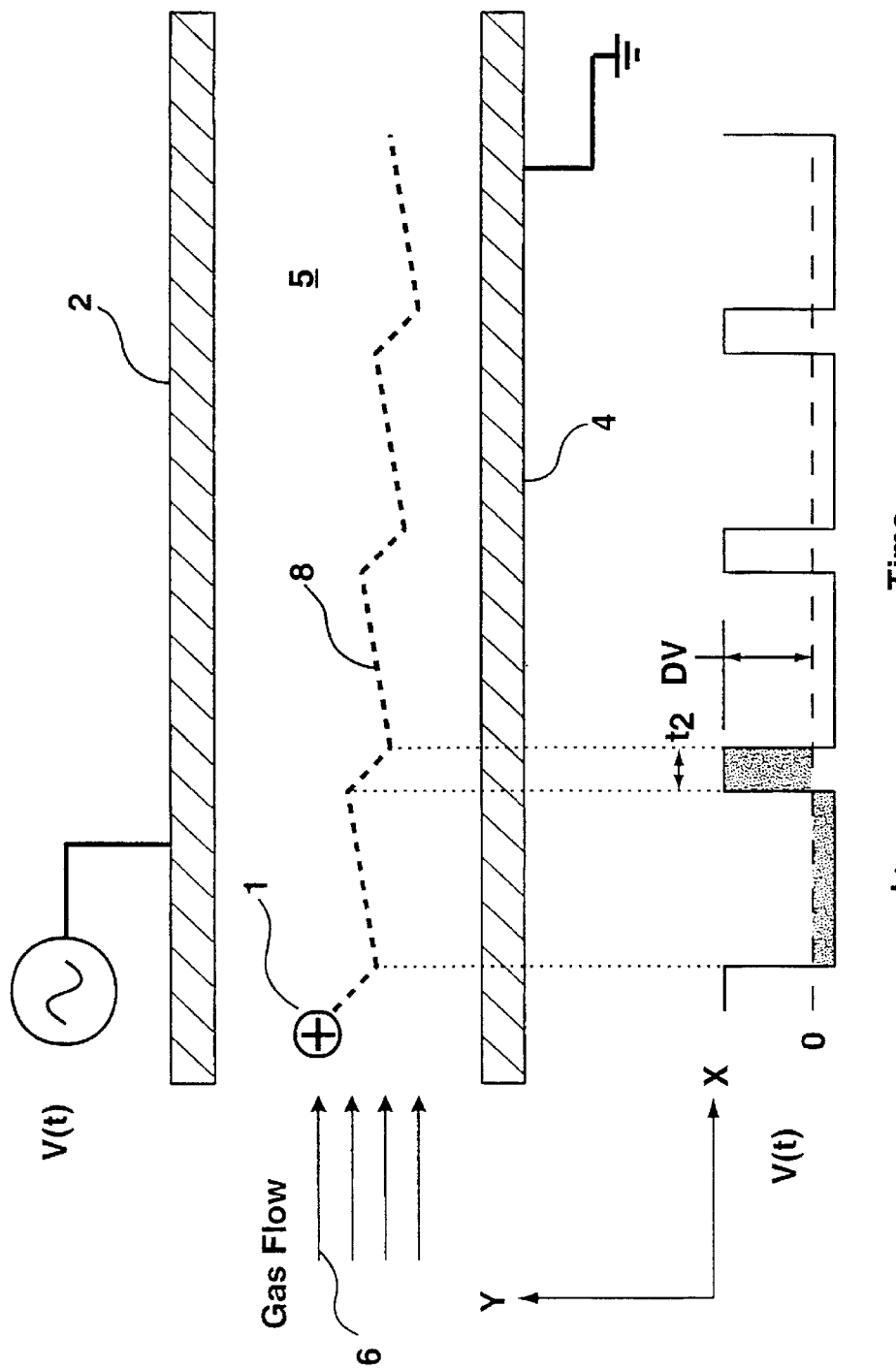
FIG. 2 illustrates the trajectory of an ion between two parallel plate electrodes under the influence of the electrical potential V(t)

Referring to FIG. 1, three examples of changes in ion mobility as a function of the strength of an electric field are shown: the mobility of type A ions increases with increasing electric field strength; the mobility of type C ions decreases; and the mobility of type B ions increases initially before decreasing at yet higher fields. The separation of ions in FAIMS is based upon these changes in mobility at high electric fields. Consider an ion 1, for example a type A ion shown in FIG. 1, that is being carried by a gas stream 6 between two spaced apart parallel plate electrodes 2, 4 as shown in FIG. 2. The space between the plates 2, 4 defines an analyzer region 5 in which the separation of ions may take place. The net motion of the ion 1 between the plates 2, 4 is the sum of a horizontal x-axis component due to a flowing stream of gas 6 and a transverse y-axis component due to the electric field between the plates 2, 4. (The term "net" motion refers to the overall translation that the ion 1 experiences, even when this translational motion has a more rapid oscillation superimposed upon it.) One of the plates is maintained at ground potential (here, the lower plate 4) while the other (here, the upper plate 2) has an asymmetric waveform, V(t), applied to it. The asymmetric waveform V(t) is composed of a high voltage component, $V_1$, lasting for a short period of time $t_2$ and a lower voltage component, $V_2$, of opposite polarity, lasting a longer period of time $t_1$. The waveform is synthesized such that the integrated voltage-time product (thus the field-time product) applied to the plate during a complete cycle of the waveform is zero (i.e., $V_1 t_2 + V_2 t_1 = 0$); for example +2000 V for 10 µs followed by −1000 V for 20 µs. FIG. 2 illustrates the ion trajectory 8 (as a dashed line) for a portion of the waveform shown as V(t). The peak voltage during the shorter, high voltage portion of the waveform will be called the "dispersion voltage" or DV in this disclosure. During the high voltage portion of the waveform, the electric field will cause the ion 1 to move with a transverse velocity component $v_1 = K_h E_{high}$, where $E_{high}$ is the applied field, and $K_h$ is the high field mobility under ambient electric field, pressure and temperature conditions. The distance travelled will be $d_1 = v_1 t_2 = K_h E_{high} t_2$, where $t_2$ is the time period of the applied high voltage. During the longer duration, opposite polarity, low voltage portion of the waveform, the velocity component of the ion will be $v_2 = K E_{low}$, where K is the low field ion mobility under ambient pressure and temperature conditions. The distance travelled is $d_2 = v_2 t_1 = K E_{low} t_1$. Since the asymmetric waveform ensures that $(V_1 t_2) + (V_2 t_1) = 0$, the field-time products $E_{high} t_2$ and $E_{low} t_1$ are equal in magnitude. Thus, if $K_h$ and K are identical, $d_1$ and $d_2$ are equal, and the ion 1 will be returned to its original position along the y-axis during the negative cycle of the waveform (as would be expected if both portions of the waveform were low voltage). If at $E_{high}$ the mobility $K_h > K$, the ion 1 will experience a net displacement from its original position relative to the y-axis. For example, positive ions of the type A shown in FIG. 1 will travel further during the positive portion of the waveform (i.e., $d_1 > d_2$) and the type A ion 1 will migrate away from the upper plate 2 (as illustrated by the dashed line 8 in FIG. 2). Similarly, ions of type C will migrate towards the upper plate 2.

If an ion of type A is migrating away from the upper plate 2, a constant negative dc voltage can be applied to this plate 2 to reverse, or "compensates" for this transverse drift. This dc voltage, called the "compensation voltage" or CV in this disclosure, prevents the ion 1 from migrating towards either plate 2, 4. If ions derived from two compounds respond differently to the applied high electric fields, the ratio of $K_h$ to K may be different for each compound. Consequently, the magnitude of the compensation voltage CV necessary to prevent the drift of the ion toward either plate 2, 4 may also be different for each compound. Under conditions in which the compensation voltage CV is appropriate for transmission of one compound, the other will drift towards one of the plates 2, 4 and subsequently be lost. The speed at which the compound will move to the wall of the plates 2, 4 depends on the degree to which its high field mobility properties differ from those of the compound that will be allowed to pass under the selected condition. A FAIMS instrument or apparatus is an ion filter capable of selective transmission of only those ions with the appropriate ratio of $K_h$ to K.

The term FAIMS, as used in this disclosure, refers to any device which can separate ions via the above described mechanism, whether or not the device has focussing or trapping behaviour.

Improvements to FAIMS

The FAIMS concept was first shown by Buryakov et. al. using flat plates as described above. Later, Carnahan et. al. improved the sensor design by replacing the flat plates used to separate the ions with concentric cylinders (see B. Carnahan, S. Day, V. Kouznetsov, M. Matyjaszczyk, and A. Tarassov, Proceedings of the 41st ISA Analysis Division Symposium, Framingham, Mass., Apr. 21–24, 1996, p. 85; U.S. Pat. No. 5,420,424 issued to Carnahan et al.). The concentric cylinder design has several advantages including higher sensitivity than the flat plate configuration (see R. W. Purves, R. Guevremont, S. Day, C. W. Pipich, and M. S. Matyjaszczyk, Rev. Sci. Instrum., 69, 4094 (1998)).

As mentioned earlier, an instrument based on the FAIMS concept has been built by Mine Safety Appliances Company (MSA). The MSA instrument uses the concentric cylinder design and is described further below. (For the purposes of this disclosure, the MSA instrument is referred to as FAIMS-E, where E refers to an electrometer or electric current detection device.)

One previous limitation of the cylindrical FAIMS technology (see D. Riegner, C. Harden, B. Carnahan, and S. Day, Proceedings of the 45th ASMS Conference on Mass Spectrometry and Allied Topics, Palm Springs, Calif., Jun. 1–5, 1997, p. 473; and B. Carnahan, S. Day, V. Kouznetsov, M. Matyjaszczyk, and A. Tarassov, Proceedings of the 41st ISA Analysis Division Symposium, Framingham, Mass., Apr. 21–24, 1996, p. 85) was that the identity of the peaks appearing in the FAIMS-E CV spectra could not be unambiguously confirmed due to the unpredictable changes in $K_h$ at high electric fields.

Thus, one way to extend the capability of instruments based on the FAIMS concept, such as the FAIMS-E instrument, is to provide a way to determine the make-up of the FAIMS-E CV spectra more accurately, for example, by introducing ions from the FAIMS-E device into a mass spectrometer for mass-to-charge (m/z) analysis.

In addition, it has been found that a modified FAIMS instrument, or any similar instrument, can be used in a new method of separating isomers and different conformations of gaseous phase ions. The present invention is directed to a new method of separating isomers and different conformations of ions and illustrates the method by several examples. Details of the method of the present invention are described below.

Electrospray Ionization

ESI is one of several related techniques that involves the transfer of ions (which can be either positively or negatively charged) from liquid phase into the gas-phase. Kebarle has described four major processes that occur in electrospray ionization (intended for use in mass spectrometry): (1) production of charged droplets, (2) shrinkage of charged droplets by evaporation, (3) droplet disintegration (fission), and (4) formation of gas-phase ions (Kebarle, P. and Tang, L. Analytical Chemistry, 65 (1993) pp. 972A–986A). In ESI, a liquid solution (e.g. 50/50 w/w water/methanol) is passed through a metal capillary (e.g., 200 µm outer diameter and 100 µm ID) which is maintained at a high voltage to generate the charged droplets, say +2000 V (50 nA) for example. The liquid samples can be pumped through at, say, 1 µL/min. The high voltage creates a very strong, non-constant electric field at the exit end of the capillary, which nebulizes the liquid exiting from the capillary into small charged droplets and electrically charged ions by mechanisms described by Kebarle and many others. Several related methods also exist for creating gas-phase ions from solution phase. Some examples of these methods include ionspray, which uses mechanical energy from a high velocity gas to assist in nebulization; thermospray, which applies heat instead of a voltage to the capillary; and nanospray, which uses small ID capillaries. In this disclosure, the term ESI is used to encompass any technique that creates gas-phase ions from solution.

Modified FAIMS-E

As a first step, the FAIMS-E device designed and built by Mine Safety Appliances Company was modified to permit the introduction of ions using ESI. The inventors believe that the coupling of an ESI source together with a FAIMS-E device is not obvious as it is known that ions produced by ESI have a high degree of solvation, and that a FAIMS-E device may not function properly when exposed to high levels of solvent vapour. The inventors have developed various practical embodiments of an apparatus that combines an ESI source together with a FAIMS device to show that such coupling is possible.

Figure 3A:
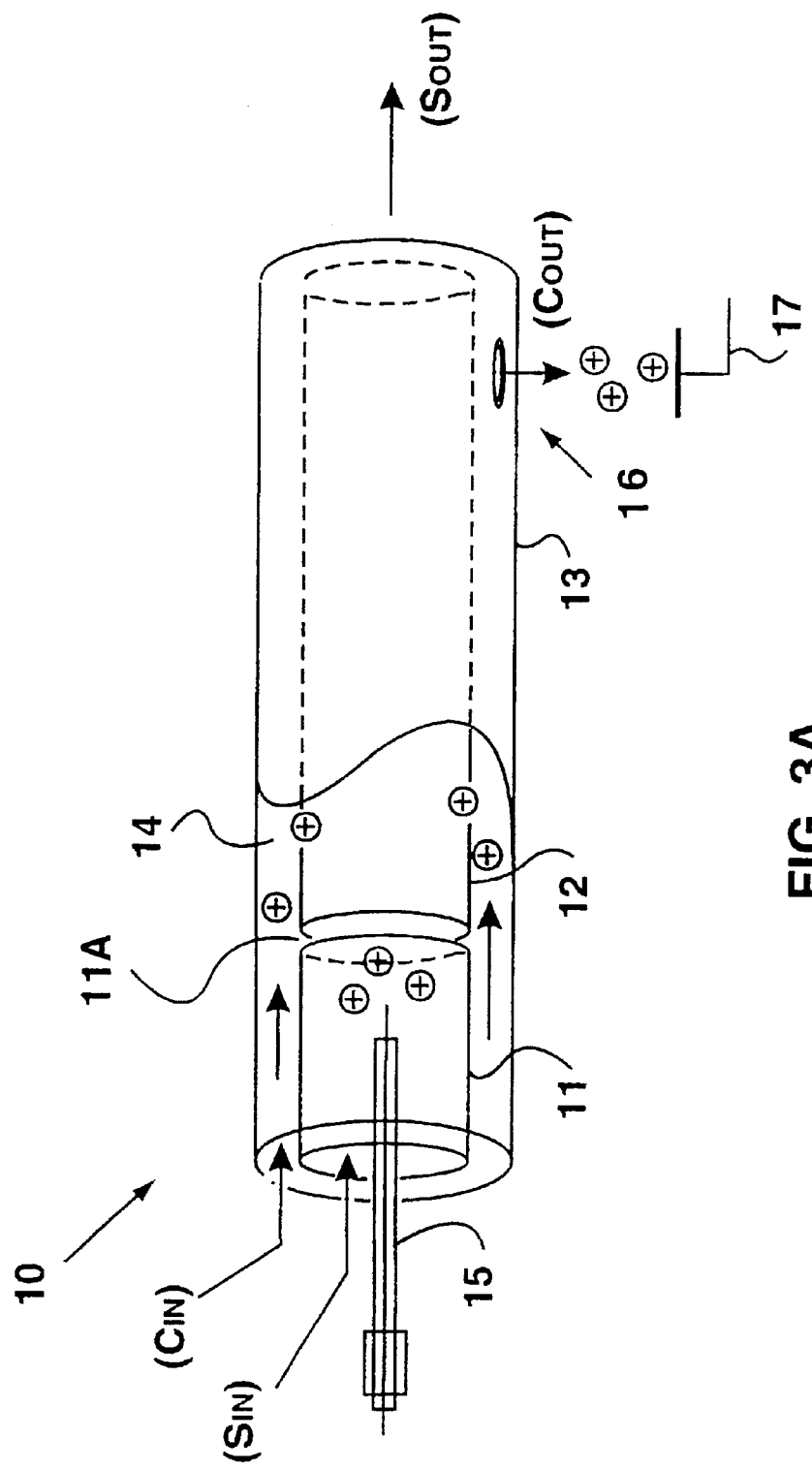
FIGS. 3A and 3B show schematically an embodiment of a modified FAIMS device.
Figure 3B:
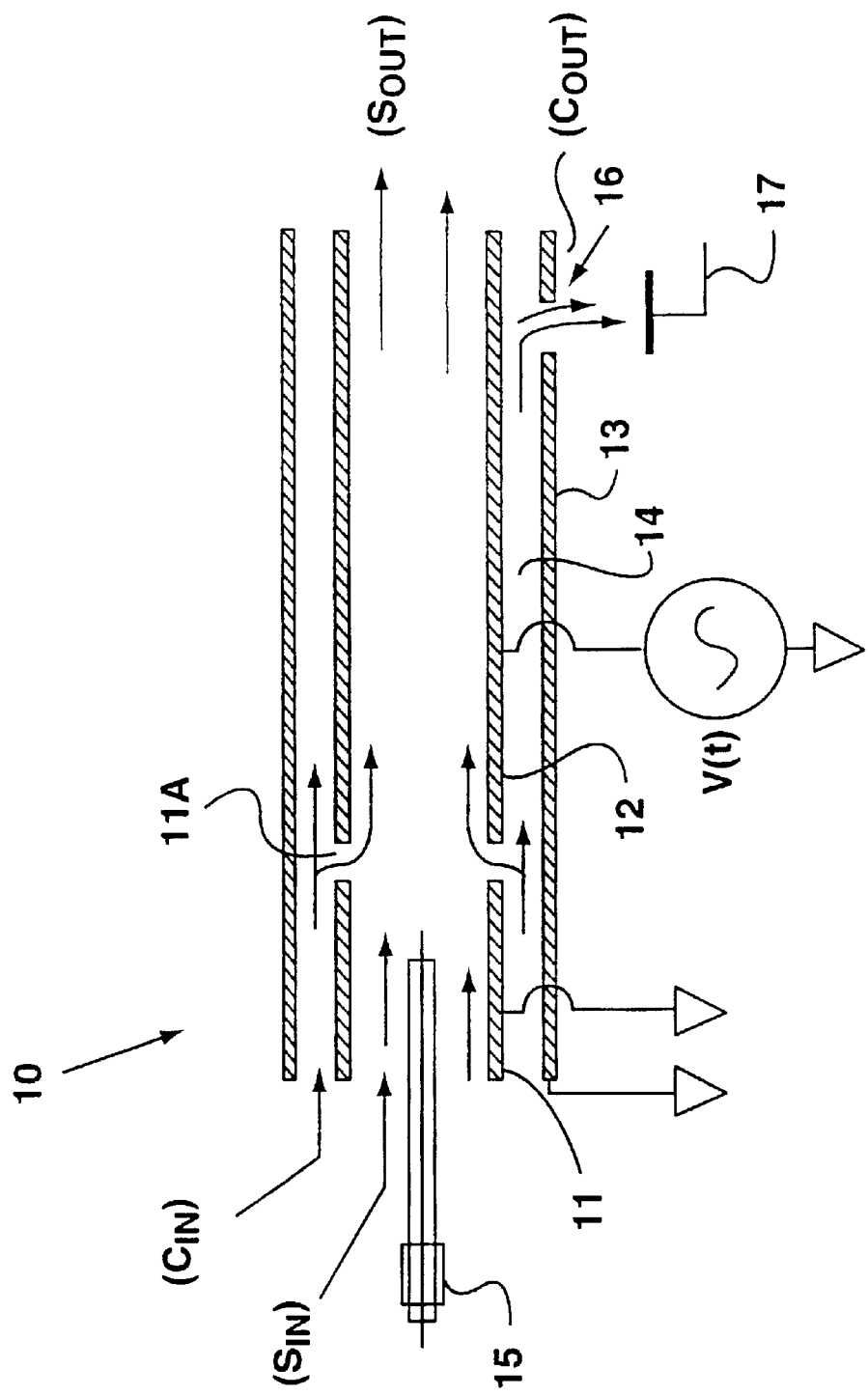

One example is the modified FAIMS-E device 10 shown schematically in 3-dimensional view in FIG. 3A and in cross section in FIG. 3B. The FAIMS-E apparatus 10 is composed of two short inner cylinders or tubes 11, 12 which are axially aligned and positioned about 5 mm apart, and a long outer cylinder 13 which surrounds the two inner cylinders 11, 12. The inner cylinders 11, 12 (12 mm inner diameter, 14 mm outer diameter), are about 30 mm and 90 mm long, respectively, while the outer cylinder 13 (18 mm inner diameter, 20 mm outer diameter) is about 125 mm long. Ion separation takes place in the 2 mm annular space of FAIMS analyzer region 14 between the long inner cylinder 12 and the outer cylinder 13. To produce ions using electrospray ionization (ESI), for introduction into the FAIMS analyzer region 14 of the FAIMS device, the metal capillary of the ESI needle 15 was placed along the central axis of the shorter inner cylinder 11, terminating about 5 mm short of the gap or ion inlet between the two inner cylinders 11, 12. The positioning of the ESI needle 15 shown in FIGS. 3(A) and 3(B) differs from the positioning of the ionization source found in the MSA FAIMS-E device in that the ESI needle 15 does not extend through the long inner cylinder 12 to which the asymmetric waveform V(t) is typically applied. By introducing the ESI needle 15 from the opposite end of the FAIMS-E, i.e. through the short inner cylinder 11, and not positioning the tip of the ESI needle 15 too close to the long inner cylinder 12, the performance of the ESI needle 15 is not compromised by the asymmetric waveform V(t), which would be the case if the ESI needle 15 was positioned within the long inner cylinder 12 (as disclosed in U.S. Pat. No. 5,420,424).

As explained above, the FAIMS-E device 10 can be considered as an ion "filter", with the capability of selectively transmitting one type of ion out of a mixture. If a mixture of ions is presented continuously to the entrance of the FAIMS analyzer region 14, for example by an ESI needle 15, and the ions are carried along the length of the analyzer 14 by a flowing gas under conditions in which no voltages are applied to either the inner cylinder 12 or outer cylinder 13 (i.e. the electrodes are grounded), some finite level of transmission for every ion is expected, albeit without any separation.

It might be expected that the detected current of any selected ion in this mixture should never exceed the current for that ion when it is transmitted through the device 10 in the no-voltages condition. It might also be expected that application of high voltages (i.e. application of transverse fields, perpendicular to the gas flows) designed to yield ion separation should not increase the ion transmission, but should decrease transmission through collisions with the walls of the cylinders 12, 13. That is, the asymmetric waveform might effectively narrow the "width" of the FAIMS analyzer region 14, and therefore should decrease the ion transmission. However, contrary to this prediction, experiments conducted by the inventors and described in this disclosure have shown that the sensitivity of ion detection in the cylindrical geometry FAIMS-E 10 increases as the voltage amplitude of the asymmetric waveform V(t) is increased. As will be explained below, these unusual observations suggest that atmospheric pressure ion focussing is occurring in the FAIMS analyzer region 14.

Still referring to FIGS. 3A and 3B, four gas connections to the FAIMS-E apparatus 10 are shown. Compressed gas (e.g. air or nitrogen) is passed through a charcoal/molecular sieve gas purification cylinder (not shown) into the FAIMS-E 10 through carrier in ($C_{in}$) and/or sample in ($S_{in}$) ports. The gas exits the FAIMS-E 10 via the carrier out ($C_{out}$) and/or sample out ($S_{out}$) ports. All four gas flow rates can be adjusted. Non-volatile analytes are typically introduced into the FAIMS-E 10 using an ESI needle 15. Alternatively, volatile analytes may be introduced into the FAIMS-E 10 through the $S_{in}$ line, and a portion may be ionized as the compound(s) pass by a corona discharge needle.

Still referring to FIGS. 3A and 3B, the outer cylinder 13 of the FAIMS-E apparatus 10, and the shorter inner cylinder 11, are typically held at an adjustable electrical potential ($V_{FAIMS}$). $V_{FAIMS}$ is usually ground potential in FAIMS-E. During operation, a high frequency high voltage asymmetric waveform is applied to the long inner cylinder 12 to establish the electric fields between the inner and outer cylinders 12, 13. In addition to this high frequency (e.g., 210 kHz) high voltage waveform a dc offset voltage (i.e. the compensation voltage CV added to FAIMS) is applied to the long inner cylinder 12. This leads to the separation of ions in the FAIMS analyzer region 14 in the manner discussed earlier.

Still referring to FIGS. 3A and 3B, some of the ions produced by the ionization source are carried by the gas stream along the length of the annular space between the outer cylinder 13 and the long inner cylinder 12, also referred to as the FAIMS analyzer region 14. If the combination of DV and CV are appropriate, and the ion is not lost to the tube walls, a series of openings or ion outlets 16 near the downstream end of the outer cylinder 13 allow the ions to be extracted to an electrical current detector 17 which is biased to about −100 V. (Note that here the carrier gas also exits from the ion outlet 16.)

Figure 4:
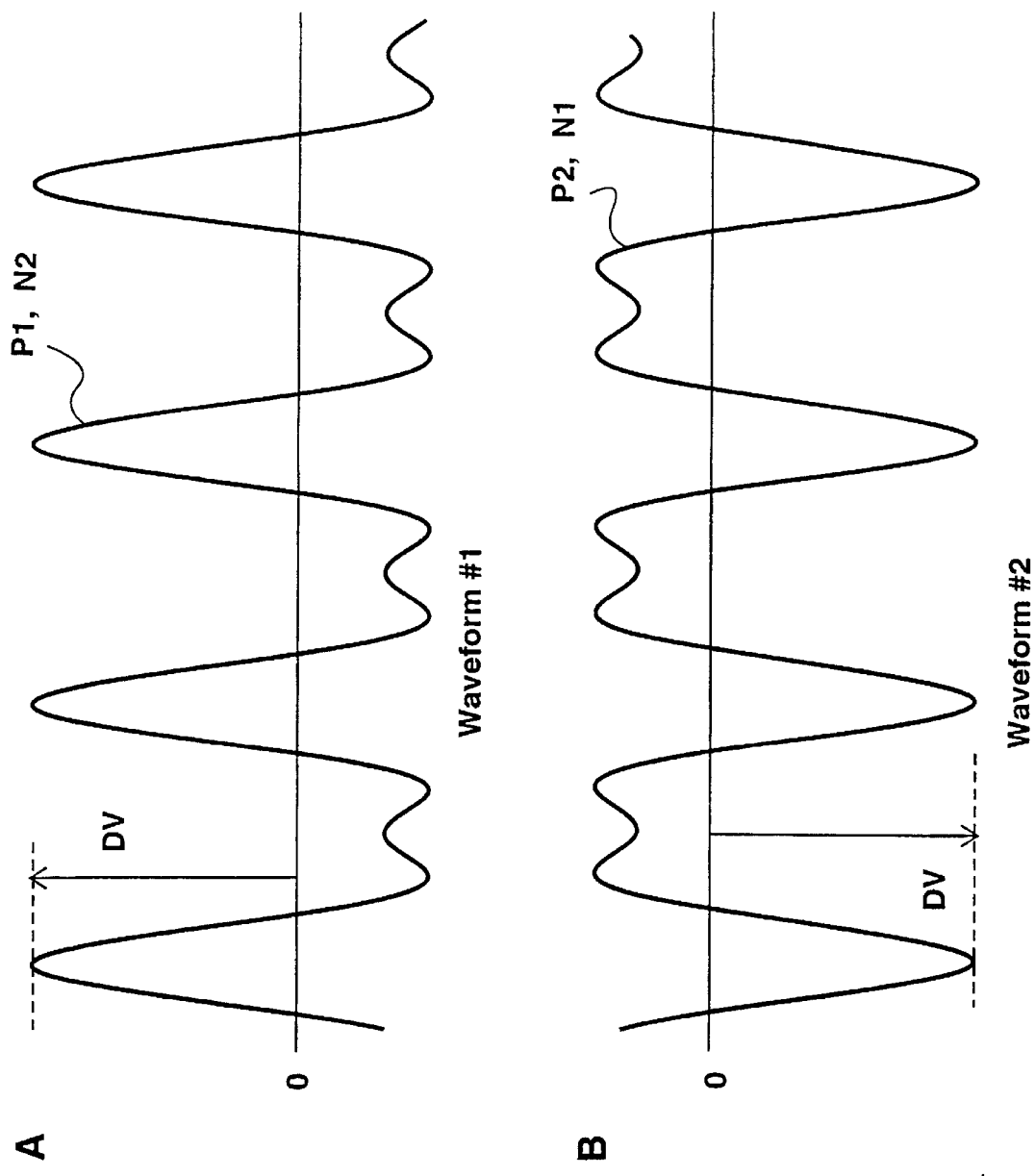
FIG. 4 illustrates two opposite waveform modes which may be used with the apparatus of FIGS. 3A and 3B.

In practice, the simplified square wave version of V(t) shown in FIG. 2 cannot be used because of the electrical power demands that such a wave would place on the waveform generator. The actual waveforms V(t) appear in FIG. 4. These waveforms are produced by the electronic addition of a sine wave and its harmonic of twice the frequency. As shown in FIG. 4, the FAIMS-E apparatus 10 operates using one of the two waveform modes (with the waveform applied to the inner cylinder). These reversed polarity waveform modes do not yield "reversed polarity" CV spectra as might be expected. This is because the reversal of polarity in this manner also creates a mirror image effect of the ion focussing behaviour of FAIMS. The result of such polarity reversal is that the ions are not focussed, but rather collide with the walls of the cylinders 12, 13. The mirror image of a focussing valley is a hill-shaped potential surface. (This characteristic, and the various "modes" of operation of FAIMS, is discussed further below.)

FAIMS-MS

As discussed earlier, one way to extend the functionality of FAIMS devices is to couple them together with a mass spectrometer. The use of a mass spectrometer together with a FAIMS device is advantageous because the mass spectrometer facilitates a mass-to-charge (m/z) analysis to determine the make-up of CV spectra more accurately. One possible FAIMS-MS embodiment is described here.

Figure 5A:
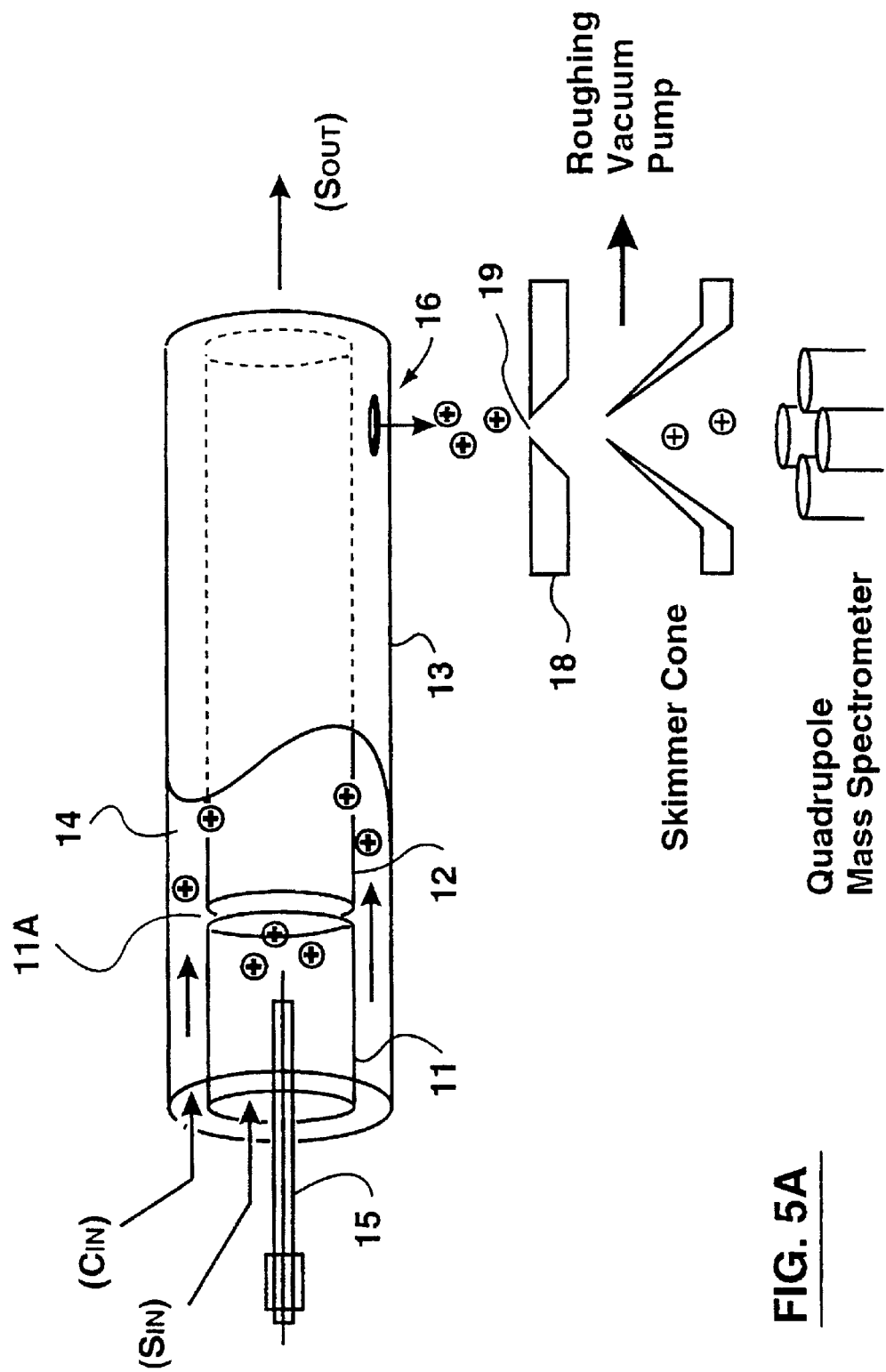

Referring to FIGS. 5A and 5B, the coupling of FAIMS and a mass spectrometer (FAIMS-MS 20) is shown schematically. The FAIMS-MS 20 of FIGS. 5A and 5B, and the FAIMS-E 10 shown in FIGS. 3A and 3B, differ significantly only at the detection end of the instrument. In accordance with the invention, the electrometer 17 has been replaced by a sampler cone 18, placed at the end of the FAIMS cylinders 12, 13 as is shown in a simplified form in FIG. 5B. The diameter of the orifice 19 in the sampler cone 18 is approximately 250 µm. The gas flows in the FAIMS-MS 20 are analogous to those in the FAIMS-E 10 except that the $C_{out}$ is divided into two components, namely the original $C_{out}$ and the flow through the orifice 19 into the mass spectrometer. The electrical waveforms applied to the long inner cylinder 12 are identical to those used in the FAIMS-E apparatus 10. The sampler cone 18 may be electrically insulated from the other components so a separate voltage OR can be applied to it. Furthermore, a voltage can be applied to the cylinders of the entire FAIMS unit ($V_{FAIMS}$) for the purpose of enhancing the sensitivity of the FAIMS-MS.

FIG. 5B shows the FAIMS cylinders 12, 13 at a 45 degree angle in relation to the sampler cone 18 of the mass spectrometer. FIG. 5A showed the FAIMS cylinders 12, 13 at a 90 degree angle in relation to the sampler cone 18. The way (i.e., the angle between the two tubes of the FAIMS and the sampler cone 18) in which the ions are extracted from the cylinders 12, 13 of the FAIMS-MS 20 into the mass spectrometer is not limited to these angles. Furthermore, the location in which the ions are extracted from the two tubes can also be changed. That is, the ions can be extracted anywhere along the separation region of the FAIMS.

Ion Focussing

Figure 6A:
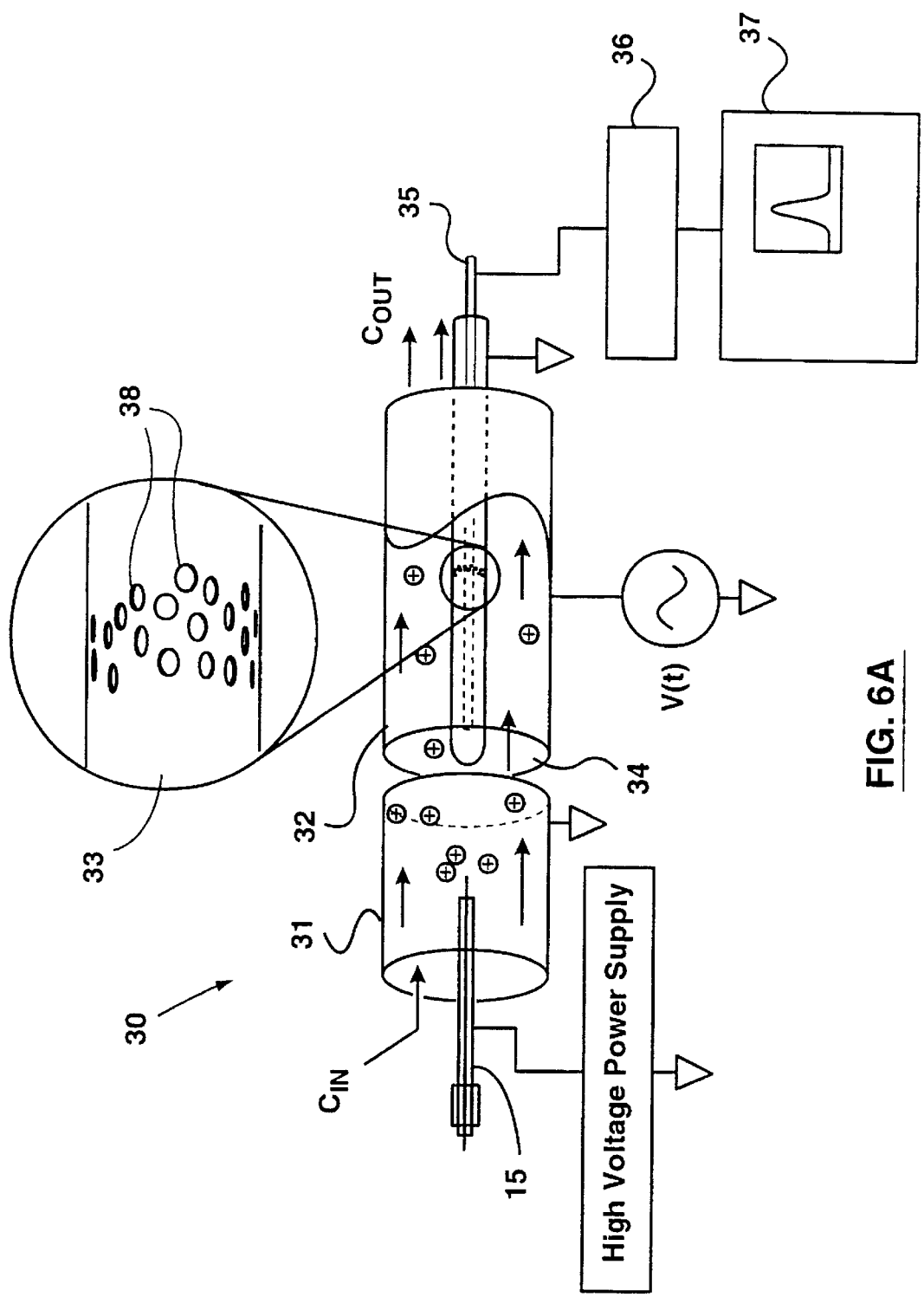

Referring now to FIGS. 6A and 6B, to demonstrate the focussing effect referred to above, a special FAIMS instrument was designed by the inventors and constructed to measure the ion distribution between the two cylinders (outer and inner cylinders) of a FAIMS device. This instrument will be referred to in this disclosure as the FAIMS-R1-prototype 30 and is illustrated schematically in FIGS. 6A and 6B. Ions were generated inside of an electrically grounded cylinder 31 approximately 35 mm long and 20 mm i.d. The tip of an ionization needle 15 was typically located near the center of this tube, and at least 15 mm from the end of the FAIMS analyzer region 34. The FAIMS analyzer region 34 in this embodiment is composed of an outer tube 32 which is 70 mm long and 6 mm i.d., and which surrounds a 2 mm o.d. inner shield electrode 33. The inner shield electrode 33 is an electrically grounded stainless steel tube which is closed at the end that faces the ionization needle 15. This inner electrode 33 surrounds, and shields, an electrically isolated conductor 35 passing into its center. This innermost conductor 35 (i.e the ion collector electrode) is a collector for ions, and is connected to a fast current amplifier or electrometer 36 (e.g. Keithly model 428) and a digital storage oscilloscope 37 (e.g. LeCroy model 9450).

In the system shown in FIGS. 6A and 6B, the ions which surround the inner electrode 33 are forced inwards by a pulsed voltage. These ions travel from the FAIMS analyzer region 34 to the innermost conductor 35 through a series of 50 µm holes 38 drilled through the inner shield electrode 33. The holes drilled in the inner shield electrode 33 are positioned about 2 cm from the end facing the ionization needle 15, and are spaced about 0.5 mm apart for a distance of 10 mm on one side of the inner shield electrode 33. The holes 38 drilled in the inner shield electrode 33 are located in this manner to minimize the variability in distance between the inner shield electrode 33 and the outer cylinder 32 in the vicinity of these holes 38. It was the inventors' objective to measure the ion abundance radial profiles of the ions located in the annular space (i.e. the FAIMS analyzer region 34) between the inner shield electrode 33 and the outer electrode 32 by pulsing the ions toward the inner shield electrode 33 and through the holes 38 and against the innermost ion collector electrode 35. The time-dependent distribution of ions arriving at the innermost conductor 35 is related to the physical radial distribution of ions around the inner electrode 33. Excessive variation in the distance between the two cylinders 32, 33 would have increased the uncertainty of the ion arrival times at the innermost conductor 35, thus decreasing the spatial resolution of the measurements made with this device.

Figure 7:
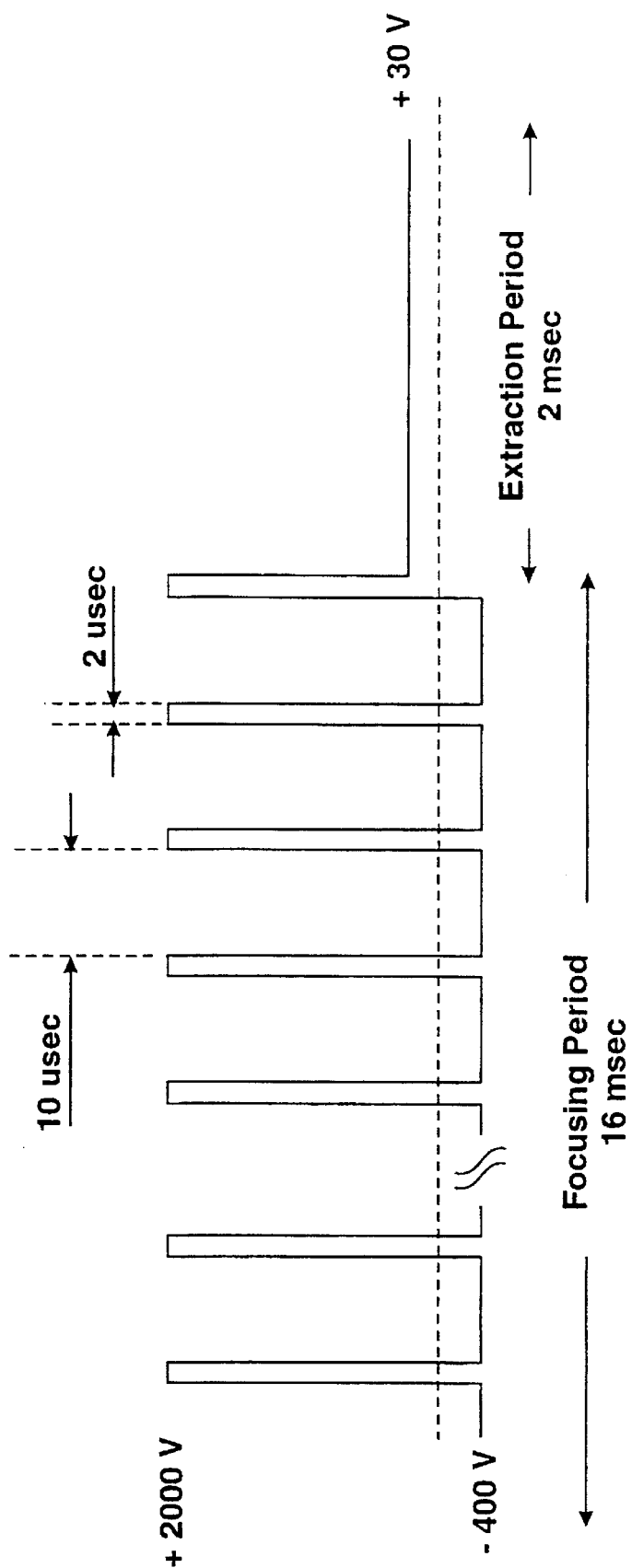
FIG. 7 illustrates the high voltage, high frequency asymmetric waveform applied to the FAIMS apparatus shown in FIGS. 6A and 6B.

Now referring to FIG. 7, the high voltage, high frequency asymmetric waveform V(t), applied to the FAIMS-R1-prototype of FIGS. 6A and 6B, is shown. The waveform is divided into two parts, the focussing period and the extraction period. The waveform was synthesized by an arbitrary waveform generator (e.g. Stanford Research Systems model DS340, not shown) and amplified by a pulse generator (e.g. Directed Energy Inc., model GRX-3.0K-H, not shown). The frequency of the waveform, and the relative duration of the high and low voltage portions of the waveform could easily be modified. Because of the high voltages, and steep risetimes of the square waves applied to this FAIMS-R1-prototype 30, the power consumption limits were severe, and waveforms in excess of about 1330 pulses (16 ms at 83,000 Hz) could not be delivered by this system without overheating electronic components of the high voltage pulse generator.

Note that, in the case of the FAIMS-R1-prototype 30, the high voltage, high frequency asymmetric waveform was applied to the outer cylinder 32 of the FAIMS-R1-prototype 30 shown in FIGS. 6A and 6B. Since all other forms of FAIMS discussed in this disclosure have the waveform applied to the inner tube or electrode, confusion may arise from the "polarity" of the waveform and the polarity of CV. In the FAIMS-R1-prototype 30 shown in FIGS. 6A and 6B, ions of type A (shown in FIG. 1) are focussed during application of the opposite polarity waveform and CV than that shown for the devices in FIGS. 3A, 3B, 5A and 5B. Nevertheless, for simplification, the polarity will be written to be the same as if the device was constructed in the same way as those of the more conventional configuration. In other words the ions transmitted during application of waveform #1 will appear with DV positive and with CV negative. (Please note, however, that the actual voltages used on the device in FIGS. 6A and 6B are DV negative and CV positive).

As was observed in the conventional parallel plate FAIMS apparatus described earlier (FIG. 2), the application of a high voltage asymmetric waveform V(t) will cause ions to migrate towards one of the FAIMS electrodes 2, 4 because of the changes in ion mobility at high electric fields (shown in FIGS. 1 and 2). This migration can be stopped by applying an electric field or compensation voltage CV in a direction to oppose the migration. For the FAIMS-R1-prototype 30 of FIGS. 6A and 6B, this CV was applied to the same electrode as the high voltage asymmetric waveform (i.e. the outer electrode 32), and was added to the waveform as a small dc bias (up to ±50 V). At an appropriate combination of DV, and compensation voltage CV, a given ion will pass through the FAIMS device 30. The unit therefore acts like an ion filter. It is possible to fix conditions such that a single type of ion is isolated in the FAIMS analyzer 34 although a mixture flows uniformly out of the exit of the FAIMS device 30 although a mixture of ions are presented to the inlet of the FAIMS analyzer region 34.

The second part of the waveform shown in FIG. 7 (i.e. the extraction period) was used to pulse the ions out of the FAIMS analyzer region 34 between the outer electrode 32, and the inner shield electrode 33 (shown in FIGS. 6A and 6B). At the end of the focussing period, i.e. after 16 ms of waveform, the asymmetric waveform was replaced by a constant dc bias of approximately +30 V. This caused the ions from the annular space 34 between the outer electrode 32 and the inner shield electrode 33 to move in the direction of the inner shield electrode 33. A detector bias of −5 V, applied to innermost ion collector electrode 35, helped to carry the ions from the vicinity of the holes 38 in the inner shield electrode 33, through the holes 38 and into contact with the innermost ion collector electrode 35. The +30 V bias created an electric field of approximately 150 V/cm across the FAIMS analyzer region 34 and most ions located within this region 34 travelled across the 2 mm space in about 1 ms. The ion current due to the arrival of ions at the center inner shield electrode 33 can be predicted. For example, if only one type of ion, with mobility of 2.3 $cm^2$/V-s, e.g., $(H_2O)_nH^+$ at ambient temperature and pressure conditions, was located in the FAIMS analyzer region 34, and if this ion was distributed evenly in the space, an approximately square-topped signal lasting approximately 0.6 ms should be observed. Deviation from this expected ion arrival profile would suggest that the ions were distributed in non-uniform profile across the FAIMS analyzer region 34 between the outer and inner cylinders of the FAIMS device 30.

Still referring to FIGS. 6A, 6B, and 7, the FAIMS-R1-prototype 30 was operated as follows. A 2 L/min flow of purified air, Carrier Gas In (Cin), was passed into the cylinder 31 housing the ionization needle 15. Approximately 2000 V was applied to the needle 15, and the voltage was adjusted to produce a stable ionization current. The high voltage asymmetric waveform V(t) was applied to the outer FAIMS cylinder 32 for approximately 16 ms; this was followed by a 2 ms extraction pulse (FIG. 7). The ion current striking the innermost ion collecting electrode 35 was detected and displayed on a digital oscilloscope 37. A measurement would typically consist of 100 averaged spectra, collected at a rate of approximately 5 Hz. Many experimental parameters were varied, including gas flow rates, the voltages of the asymmetric waveform V(t), the dc voltage applied to the outer electrode CV, and the extraction voltage.

Figure 8:
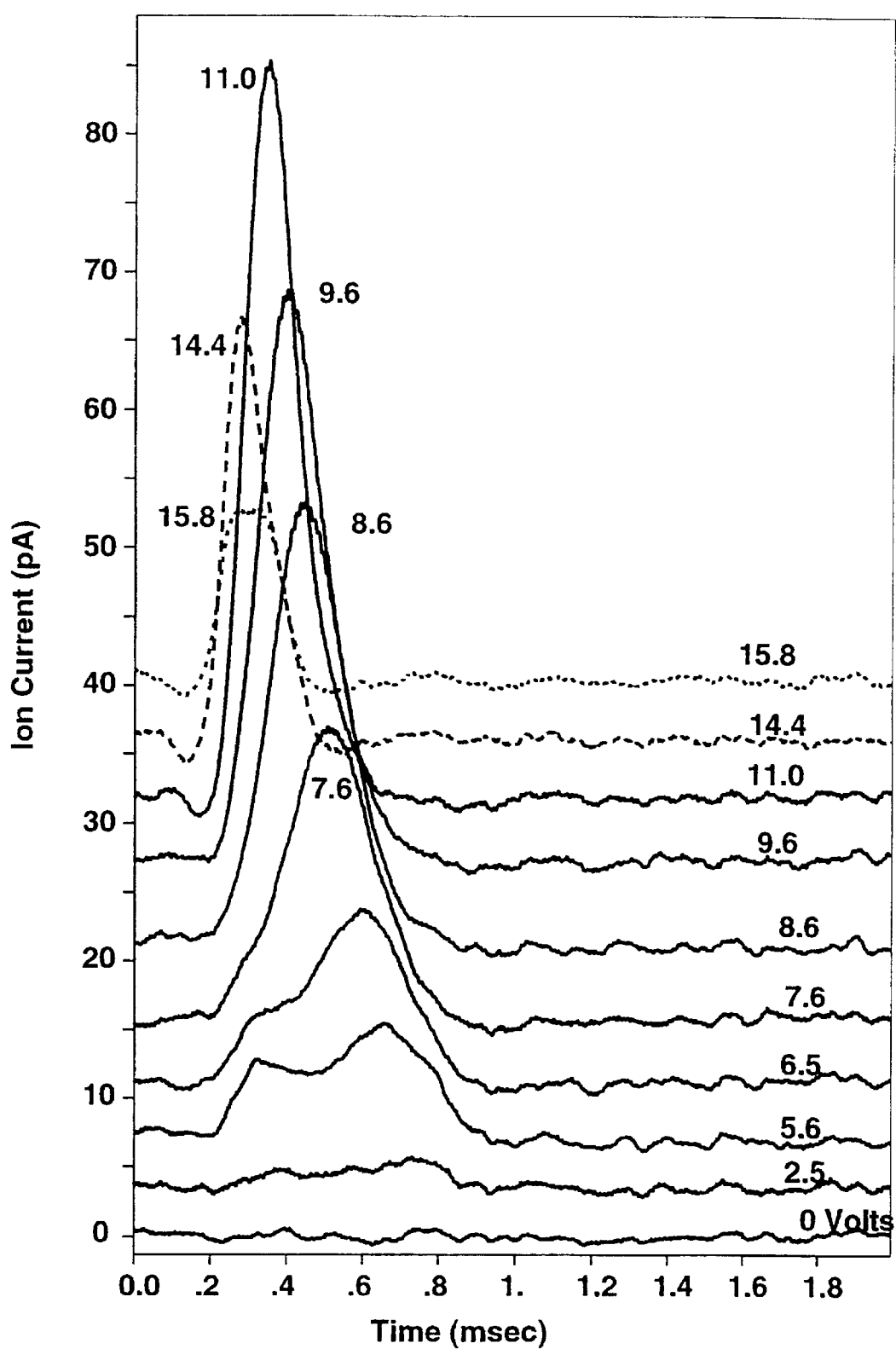
FIG. 8 illustrates varying ion arrival time profiles at the innermost ion collector electrode of the FAIMS apparatus in FIGS. 6A and 6B.

FIG. 8 illustrates the ion arrival times at the innermost ion collector electrode 35 observed by conducting these experiments. Each trace was recorded with 2500 V applied DV, but with variable CV voltages. As can be seen, during application of DV and CV, the radial distribution of ions is not uniform across the annular space of the FAIMS analyzer region 34. For example, at CV near −11 V, the ions are focussed into a narrow band near the inner electrode 33, and therefore are detected as a high intensity pulse occurring very early after the extraction voltage has been applied. At low CV, for example at −5.6 V, the ions are much more uniformly distributed between the walls of the concentric cylinders 32 33 making up the FAIMS analyzer region 34. When no electrical voltages are applied to the cylinders 32, 33, the radial distribution of ions should be approximately uniform across the FAIMS analyzer region 34 (data for this no-voltage experimental condition is not shown in this document). The experimental data shown in FIG. 8 is evidence that the ion focussing is indeed occurring in FAIMS instruments. This focussing results in the ions being focussed in a uniform "sheet" or band around the inner cylinder 33 within the FAIMS analyzer region 34. As mentioned previously, to the inventors' knowledge, this focussing effect has never been observed or explained previously.

Modes of Operation of FAIMS

The focussing and trapping of ions by the use of asymmetric waveforms has been discussed above. For completeness, the behaviour of those ions which are not focussed within the FAIMS analyzer region will be described here. As explained earlier, the ions which do not have the high field ion mobility properties suitable for focussing under a given set of DV, CV and geometric conditions will drift toward one or another wall of the device, as shown in FIG. 2. The rapidity with which they move to the wall depends on the degree to which their Kh/K ratio differs from that of the ion that might be focussed under the selected condition. At the very extreme, ions of completely the wrong property i.e. type A ion versus type C ion shown in FIG. 1, will be lost to the walls very quickly.

The loss of ions should be considered one more way. If an ion of type A (FIG. 1) is focussed at DV 2500 volts, CV −11 volts in a given geometry (for example, the FAIMS-E device of FIGS. 3A–3B), is it reasonable to expect that the ion will also be focussed if the polarity of DV and CV are reversed, i.e. DV of −2500 volts and CV of +11 volts (both applied to the inner electrode). It would seem that the reversal of polarity is a trivial exercise and the ion should be focussed, however, this is not observed. Instead, the reversal of polarity in this manner creates the mirror image effect of the ion focussing behaviour of FAIMS. The result of such polarity reversal is that the ions are not focussed, but rather are extremely rapidly rejected from the device, and collide with the walls of the cylinders 12, 13. The mirror image of a trapping valley, is a hill-shaped potential surface. The ions will slide to the center of the bottom of a trapping potential valley (2 or 3-dimensions), but will slide off of the top of a hill-shaped surface, and hit the wall of an electrode. This apparently anomalous behaviour is a consequence of the cylindrical geometry of the FAIMS-E.

This is the reason for the existence, in the FAIMS, of the independent "modes" called 1 and 2. In this disclosure, the FAIMS instrument is operated in four modes: P1, P2, N1, and N2. The "P" and "N" describe the ion polarity, positive (P) and negative (N). The waveform (FIG. 4, wave #1) with positive DV (where DV describes the peak voltage of the high voltage portion of the asymmetric waveform) yields spectra of type P1 and N2, whereas the reversed polarity (FIG. 4, wave #2, negative DV) waveform yields P2 and N1. The discussion thus far has considered positive ions but, in general, the same principles can be applied to the negative ions, as explained in the preliminary note to the Detailed Description.

Separation Experiments

Based on the FAIMS principles discussed above and the experiments conducted by the inventors to demonstrate the concept of ion focussing, the inventors have developed what is believed to be a previously unknown method for separation of isomers and different conformations of ions at substantially atmospheric pressure and substantially room temperature. Ion separation experiments involving several different types of ions are provided by way of example.

A) Leucine/Isoleucine Separation

In the prior art, there have been several attempts to distinguish the amino acids leucine (Leu) and isoleucine (Ile) using sector, ion trap and quadrupole mass spectrometry. However, since Leu and Ile are structural isomers (i.e., identical elemental composition and molecular weight), their mass spectrometric differentiation has been limited to the interpretation of fragment ion mass spectra. While differences in relative abundances of certain fragment ions can be used to unambiguously identify either of the two isomers in pure or pre-fractionated samples, mass spectrometric differentiation is incapable of selective determination within a mixture. In fact, the identification of the molecular ions of Leu and Ile, or those of their derivatives, has been demonstrated only following their chromatographic separation prior to mass spectrometric analysis. The separation of these structural isomers has been achieved using ion exchange chromatography, high performance liquid chromatography, gas chromatography, and micellar electrokinetic chromatography. In general, these chromatographic methods require 5–15 minutes for separation and produce a 5–30 second transient pulse of analyte. The length of time required for separation and the relatively short duration of the transient pulse of analyte limit this method of separation.

Based on the principles of high field asymmetric waveform ion mobility spectrometry, and based upon various experiments conducted by the inventors, a new and significantly improved method of separation of Leu and Ile has been developed and is described here.

For this experiment, the FAIMS device coupled to a mass spectrometer as shown in FIG. 5A was used. To generate negative ions, the electrospray needle was held at approximately –1900 V, giving an electrospray current of about 40 nA. The actual asymmetric waveform that was applied to the long inner cylinder of FAIMS is shown in FIG. 4 (Waveform #2). The maximum voltage of this waveform, referred to as the dispersion voltage (DV) was varied between 0 and –3300 V (which was the limit of the instrument). The frequency of the asymmetric waveform was constant at about 210 kHz. The CV, which was also applied to the long inner cylinder of the FAIMS analyzer, was scanned over specified voltage ranges.

As explained earlier, if the combination of DV and CV was appropriate, ions were not lost to the cylinder walls during their passage through the FAIMS analyzer and were transferred through an approximately 250 $\mu$m orifice 19 to the vacuum chamber of a mass spectrometer (PE SCIEX API 300 triple quadrupole). The MS orifice was electrically insulated from the FAIMS and a separate orifice voltage of –45 V was applied to it. Optionally, an offset voltage of –45 V was also applied to the entire FAIMS unit ($V_{FAIMS}$) to enhance the sensitivity of the FAIMS-MS. The skimmer cone 18A of the MS was held at ground potential and the small ring electrode normally located behind the orifice of the API 300 was not incorporated into the present interface, resulting in some loss of sensitivity for low mass ions such as Leu and Ile. Compressed air was introduced into the carrier gas inlet ($C_{in}$) at a flow rate of 3 L/min. Gas exited through the carrier gas outlet ($C_{out}$) at 2 L/min and through the sample gas out port ($S_{out}$) at 1 L/min. There was no flow through the "sample gas in" port ($S_{in}$) in this study. The pressure inside the FAIMS analyzer was kept at approximately 770 torr.

For this experiment, commercially available samples of L-leucine and L-isoleucine were obtained. All standard solutions were prepared in 9:1 methanol/water (v/v) containing 0.2 mM ammonium hydroxide.

As explained earlier, FAIMS can be operated in any one of four modes, namely P1, P2, N1 or N2, where P and N describe ion polarity (positive and negative), and "1" and "2" are indicative of instrumental conditions. In general, low mass ions (m/z<300) such as Leu and Ile are transmitted in mode 1, while larger ions are transmitted in mode 2. In the present study, the ESI source was tuned to generate negative ions. Hence, all CV and mass spectra were collected using N1 mode. The asymmetric waveform used for N1 operation is shown in FIG. 4 (Waveform #2).

Figure 9:
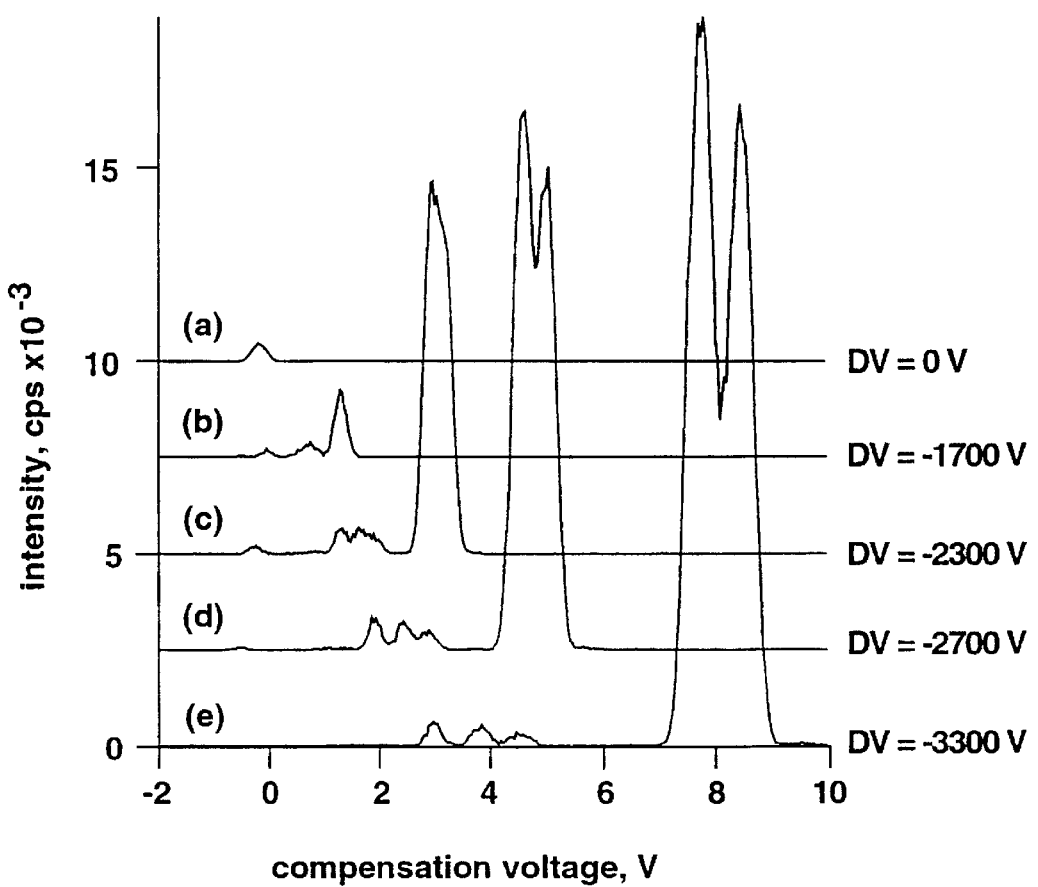
FIG. 9 shows an ion selected compensation voltage (IS-CV) spectra at five different DV values for a leucine/isoleucine mixture.

The capability of FAIMS to separate ions generated from ESI of a mixture of Leu and Ile (5 $\mu$M each) is shown in FIG. 9. In each trace, (a) to (e), the voltage of the asymmetric waveform was set, and an ion-selected CV spectrum (IS-CV) was collected by scanning the CV while monitoring m/z –130, the mass of the (M–H)$^-$ ion of both compounds (where M=$C_6H_{13}NO_2$). The dwell time and number of scans were kept constant for each spectrum. The IS-CV spectrum acquired without application of V(t) is shown in FIG. 9 trace (a). Since the transmitted ions were not subjected to the electric fields caused by V(t) within the FAIMS analyzer they have experienced no change in mobility and appear in the spectrum near CV=0 V. An increase to DV=–1700 V, FIG. 9 trace (b), results in the observation of three distinct peaks located at CV values of –0.1 V, 0.7 V and 1.3 V. Increasing DV to –2300 V, FIG. 9 trace (c), caused most of the peaks in the IS-CV spectrum to shift to higher CV values, indicating significant changes in their high field mobility terms, $K_h$. The one exception is the first peak in spectrum at CV=–0.3 V. This peak was identified as an amino acid dimer ($M_2$–H)$^-$ and is an N2 type ion, and as such is transmitted through FAIMS in N1 mode in a defocusing electric field. At DV=–2700 V, FIG. 9 trace (d), the single peak seen in FIG. 4(c) at CV 2.9 V has separated into two partially resolved peaks at CV values of 4.7 and 5.0 V. The separation of these two peaks may be improved by increasing DV to –3300 V (the limit of the power supply), as shown in FIG. 9 trace (e), giving CV values of 7.7 and 8.4 V. The position and separation of the group of smaller peaks at CV values of 2.9, 3.9 and 4.3 V in FIG. 9 trace (e) also increased. The unambiguous assignment of any of these five peaks to Leu or Ile cannot be determined from this experiment. However, the mass spectrometer ensures that all of the peaks correspond to ions with m/z –130.

Figure 10:
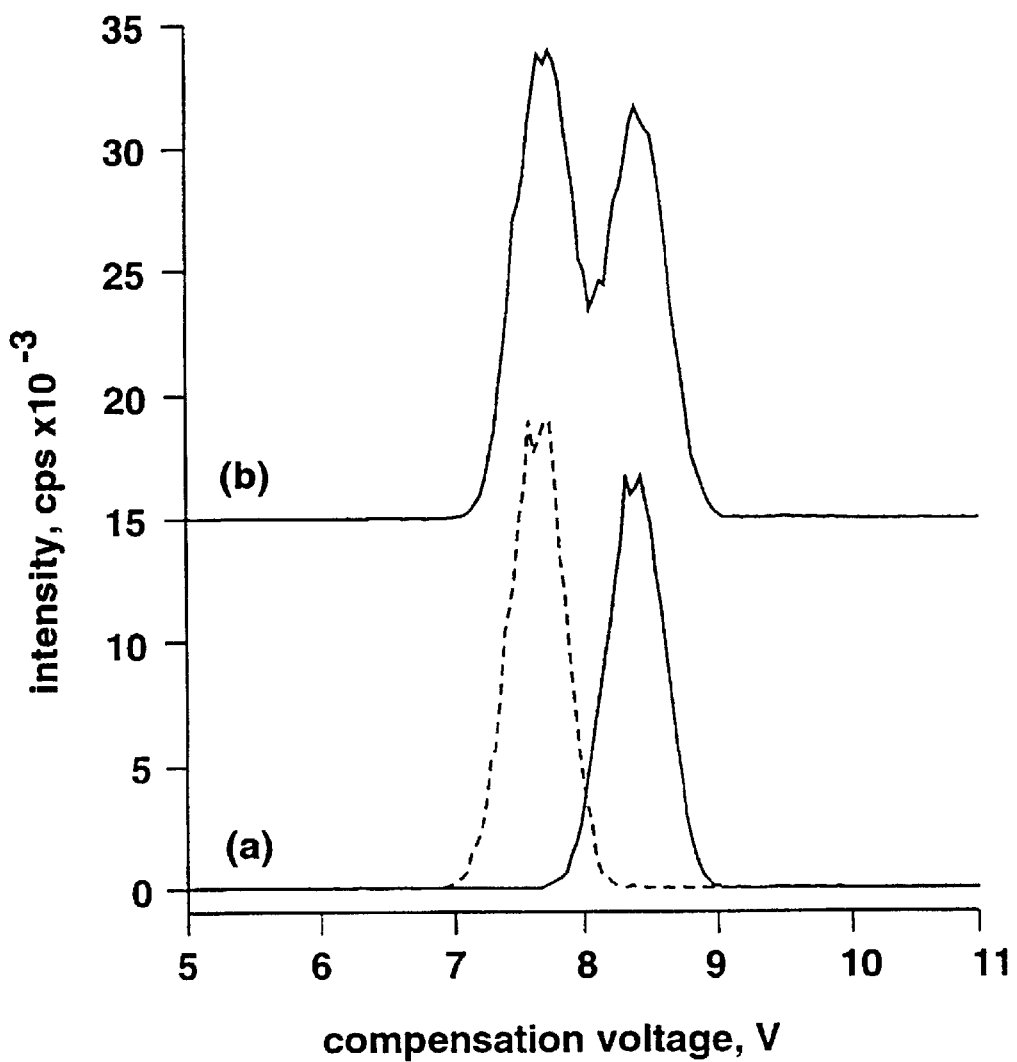
FIG. 10 trace (a) shows the IS-CV spectra, run separately, of a solution containing leucine and a solution containing isoleucine.

Identification of peaks in IS-CV spectra is analogous to using mass spectrometry as a selective detector for a chromatographic method such as CE, LC or GC. As with chromatography, it is necessary to have a set of matching standard solutions to identify the peaks in the CV spectrum. Determination of the identities of the peaks observed at CV values of 7.7 V and 8.4 V in FIG. 9 trace (e) was accomplished by collecting IS-CV spectra (m/z –130, DV=–3300 V) for 5 $\mu$M solutions of either Leu or Ile. The spectra are shown in FIG. 10 trace (a), where the dashed trace is the IS-CV spectrum of Leu and the solid trace is that of Ile. Note, FIG. 10 trace (b) is the IS-CV spectrum of the mixture, as shown previously in FIG. 9 trace (e), plotted over a narrower range of CV values. The peaks at CV values of 7.7

V and 8.4 V in the IS-CV spectrum shown in FIG. 10 trace (a) may therefore be attributed to Leu and Ile, respectively.

The three small peaks seen in FIG. 9 trace (e) at CV values of 2.9, 3.9 and 4.3 V were also present in the IS-CV spectra for both standard solutions. Identification of these peaks involved alternately tuning the FAIMS analyzer to a fixed CV value to selectively transmit one of the three ions, and collecting mass spectra using varying FAIMS-MS sampling conditions. Gentle conditions, attained by reducing the collisional voltage in the MS interface, showed that these species correspond to the following adduct ions: $(M(CH_3O(CO_2))^-$ at CV 2.9 V; $M(CH_3COO)^-$ at CV 3.9 V; and $M(NO_3)^-$ at CV 4.3 V where M is the neutral molecule of leucine or isoleucine. Under the more energetic conditions used to acquire the IS-CV spectra, these ion adducts were readily fragmented to yield the molecular ions $(M-H)^-$ of Leu and Ile at m/z −130.

As realized by the inventors, FAIMS, which continuously transmits one type of ion from a complex mixture is a significant improvement over conventional chromatographic methods of ion separation, especially when interfaced to relatively slow scanning mass spectrometers. As mentioned above, commonly used chromatographic methods for Leu and Ble are time-consuming (5–15 minute retention times) and result in narrow, finite impulses of analyte (5–30 seconds). The transient nature of these separation methods offers little flexibility in varying detection parameters and generally limits the degree to which the capabilities of the mass spectrometer may be exploited. With FAIMS, ion separation is independent of several experimental parameters associated with classical chromatography such as the stationary phase. Advantageously, problems encountered with the compatibility of LC and CE buffers (e.g. high salt content) and flow rates with the electrospray process are also eliminated.

In addition to its impressive separation ability, the FAIMS analyzer also functions to focus ions. (An experiment conducted by the inventors to show this focussing effect was described above.) A comparison of the observed ion current in FIG. 9 trace (a) and 9 trace (e) shows an increase in signal of more than two orders of magnitude when DV is increased from 0 to −3300 V. This increase in ion current is attributed to the two-dimensional atmospheric pressure ion focusing discussed in detail earlier.

Figure 11A:
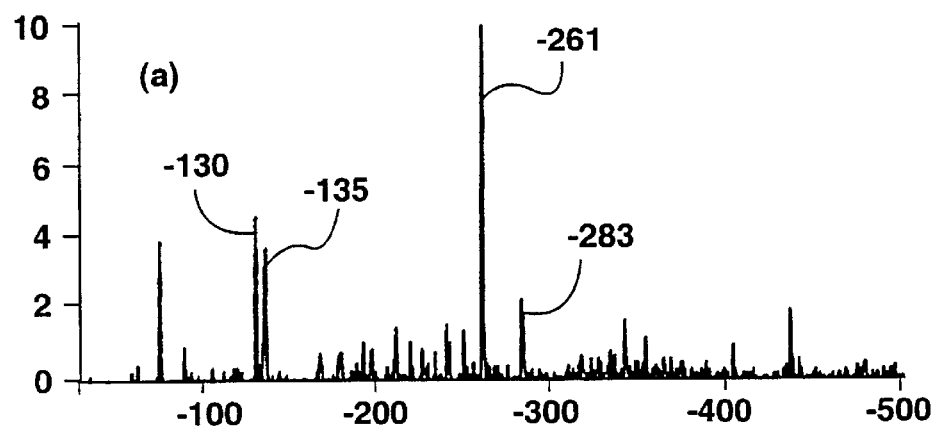
FIG. 11A shows mass spectra for a leucine/isoleucine mixture before filtering through a FAIMS analyzer.
Figure 11B:
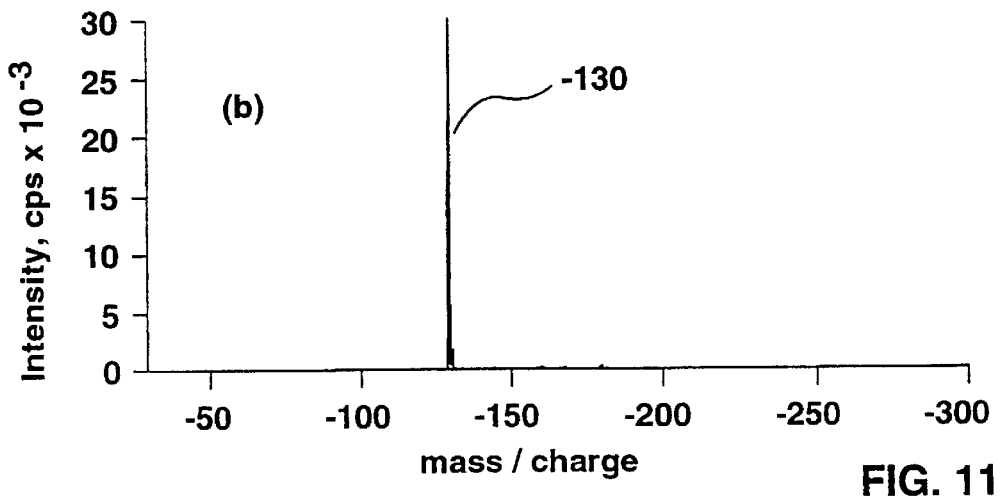
FIGS. 11B and 11C show mass spectra for a leucine/isoleucine mixture after filtering through a FAIMS analyzer at two different CV values.
Figure 11C:
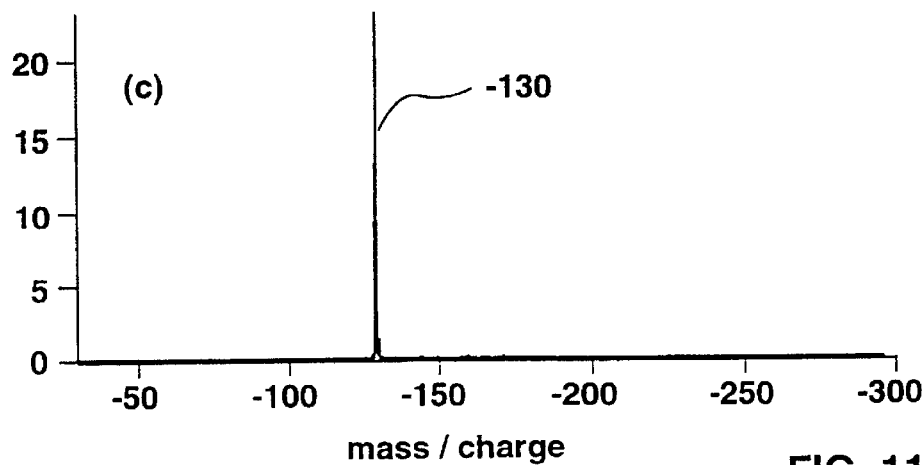

To illustrate the improvement in the mass spectra collected with FAIMS, spectra were acquired for the 5 $\mu$M Leu/Ile mixture and are shown in FIGS. 11A–11C. The spectrum acquired with FAIMS disabled (DV=0 V) and CV=0 V is shown in FIG. 11A. With no applied DV, there is no ion filtering effect, and hence no discrimination of the ions passing through the FAIMS analyzer. The mass spectrum is complex, a commonly observed and often detrimental characteristic of electrospray mass spectra in the low-mass region. Peaks attributable to $(CO_2(CH_3O)^-;$ m/z −75), oxalate (m/z −89), Leu/Ile (M−H; m/z −130), $((M_2-H)^-;$ m/z −261) and $((Na(M-H)_2^-;$ m/z −283), among others, are present. The peak observed at m/z −135 is due to an impurity in the solvent or the ammonium hydroxide buffer. From this spectrum, the signal intensity for the dimer $(M_2-H)^-$, is roughly twice that of the molecular ions of Leu and Ile at a total analyte concentration of 10 $\mu$M. At DV=−3300 V, the mass spectra collected for the same sample mixture at CV values of 7.7 V and 8.4 V, i.e., the CV values of transmission of Leu and Ile, respectively, are simple and show one intense peak at m/z −130 as shown in FIGS. 11B and 11C. The FAIMS analyzer has effectively filtered out almost all of the background ions. This filtering action of the FAIMS analyzer was observed to improve signal to background ratios (S/B) for these analytes over spectra observed in conventional ESI-MS by at least a factor of 50.

Figure 12:
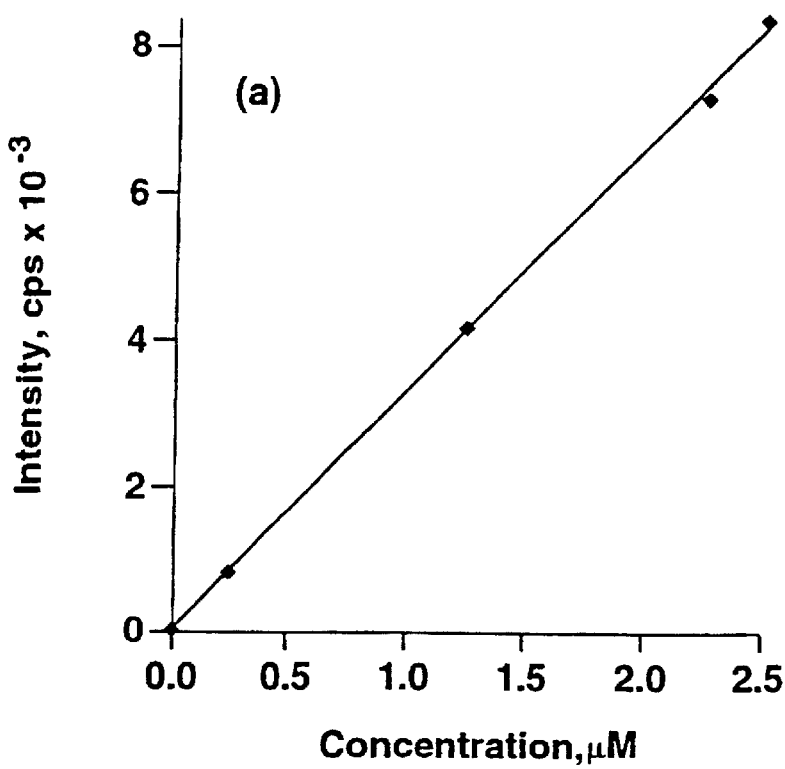
FIG. 12 shows a response curve for leucine plotted as a function of concentration.
Figure 13:
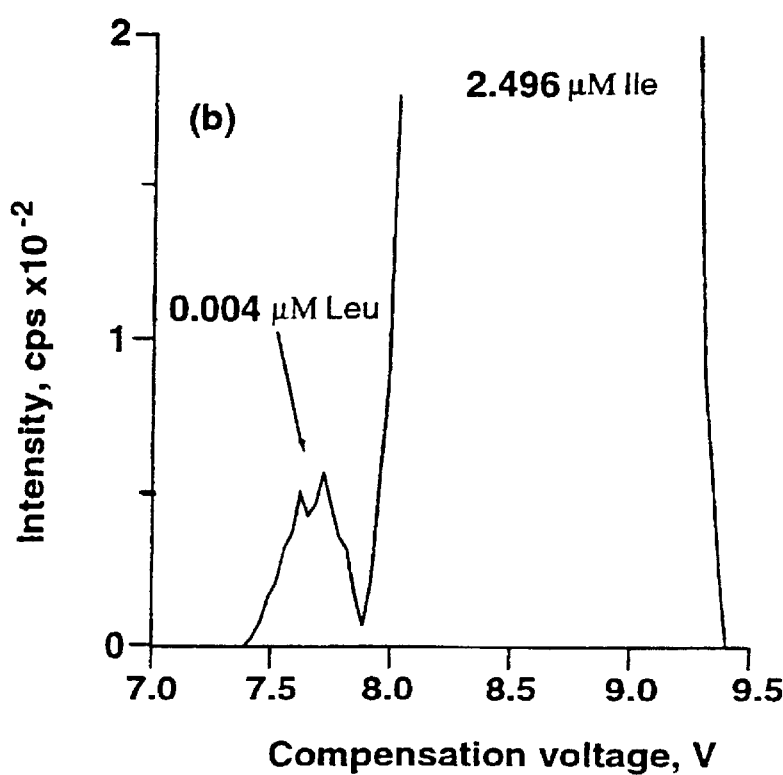
FIG. 13 shows an expanded view of an IS-CV spectrum acquired for a solution containing 0.004 $\mu$M leucine and 2.496 $\mu$M isoleucine.

The difference in the CV values required for the transmission of Leu and Ile is sufficient to permit selective monitoring of one of the species without interference from the other. This was illustrated by establishing response curves for both analytes present in a mixture. The response curve for Leu is shown in FIG. 12. The total analyte concentration (i.e., [Leu]+[Ile]) in solution was kept constant at 2.500 $\mu$M, with the individual concentrations of each analyte varying over more than two orders of magnitude (i.e., from 0.004 to 2.496 $\mu$M). The plot is linear, (y=3.3 [Leu]−0.01, $R^2$=0.9998), indicating that there is no overlap of the Leu signal from Ile when it is monitored at CV=7.7 V, the value corresponding to its peak maximum. If an overlap of Leu and Ile was present at the CV values monitored, the Leu signal at low concentration would have been most notably affected, resulting in non-linearity in the response curve. An expanded view of an IS-CV plot acquired for the solution containing 0.004 $\mu$M Leu and 2.496 $\mu$M Ile, FIG. 13, shows that the peaks are still well resolved at these concentrations. Note that the total concentration of 2.500 $\mu$M was sufficiently low that no dimer ions were observed in the mass spectra. If the concentration of dimer ions had been significant, a negative deviation in the analytical curve at high analyte concentration would have resulted.

B) Separation of Different Conformations of Gas-phase Molecular Ions Using FAIMS Recently, considerable effort has been focused on attempting to understand the relationships between the amino acid sequence, the structure, and properties of proteins. A protein is composed of a series of linked amino acids, chemically covalently bonded to each other. Since there are about 20 different types of amino acids which can be included in this chain, the first level of the description of the structure of a protein is the listing of the names of these amino acids in the sequence that they appear in the protein. This is called the amino acid sequence.

Some of the amino acids have side groups which have the capability of creating chemical bonds to the side group of another amino acids someplace else in the amino acid sequence. This creates cross-linking. This cross linking is a very important structural element of proteins, because it forces certain areas of the protein sequence to be physically in close proximity to each other, in the final protein structure.

The chains of amino acids have the capability of forming small structures including loops, and hairpin shape structures that involve only a small number of amino acids. These structures are formed because some of the side chains of the amino acids interact weakly (non-covalently) with one another, and if the appropriate amino acids are in close proximity, then these weakly held structures will spontaneously form.

Finally, the combination of all of the smaller structures, and cross-links, give the protein an overall 3 dimensional structure. This structure is called the 'conformation'. This structure can be disrupted or modified many ways. The heating of the protein will 'denature' the protein. This usually means that the protein loses its functional capability because the 3-dimensional structure has been modified. This can occur because of the breaking of a cross-linking bridge, or the disruption of small or large scale structures via addition of thermal energy to the molecule.

Conformation, therefore, describes the 3-dimensional structure of the protein. The protein has a conformation whether or not the protein is capable of performing it's normal chemical activity, i.e. native, or denatured. Some terminology which describes the 3-dimensional structure may be 'extended', 'elongated', which describes in a very non-specific way what we imagine the overall 3-dimensional structure will look like. Electrospray ionization (ESI), described above, has enabled the formation of intact gas-phase pseudo-molecular ions from large molecules, such as proteins. By coupling an ESI to a mass spectrometer (MS), ESI-MS has been used to provide information about conformations in solution. Since aqueous solutions at nearly physiological conditions are used in ESI-MS, this technique has been used to provide complementary structural information with other solution based methods such as Nuclear Magnetic Resonance (NMR).

In the prior art, information on gas-phase protein conformations has been gathered using several techniques. It has been proposed that these techniques can be divided into two general categories: chemical reactivity studies, and non-reactive studies. Chemical reactive studies, for example hydrogen-deuterium (H/D) exchange and proton transfer kinetics, examine the differences of reactivity of different conformations. Non-reactive studies use collisions with inert species to derive conformational information.

Based on the principles of high field asymmetric waveform ion mobility spectrometry discussed above, and based on experiments conducted by the inventors, a new and complementary method of measuring and studying different conformers of protein ions has been developed by the inventors and is described here.

FIG. 5A shows a schematic view of a ESI-FAIMS-MS instrument of the type that was used in this study of different conformations. The electrospray needle 15 and associated liquid delivery system were constructed by threading a 30 cm piece of fused silica capillary (50 $\mu$m i.d., 180 $\mu$m o.d.) through a 5 cm long stainless steel capillary (200 $\mu$m i.d., 430 $\mu$m o.d), with the fused silica capillary protruding about 1 mm beyond the end of the stainless steel capillary. This stainless steel capillary, in turn, protruded about 5 mm beyond the end of a larger stainless steel capillary (500 $\mu$m i.d., 1.6 mm o.d.) that was used for structural support and application of the high voltage. Solutions were delivered to the electrospray needle by a syringe pump (Harvard Apparatus model 22), at a flow rate of 1 $\mu$L/min. For the generation of positive ions, the needle was held at approximately +2200 V giving an electrospray current of about 0.03 $\mu$A. The electrospray needle was placed on the center axis of the short inner cylinder, terminating about 5 mm short of the gap 11A between the two inner cylinders 11 and 12. The electrospray ions were driven radially outward by the electric field to the analyzer region through the 5 mm gap 11A between the two inner cylinders.

A high frequency (210 kHz), high voltage (0 to 4950 V p-p), asymmetric waveform (FIG. 4) was applied to the long inner cylinder 12, thereby establishing the electric field between the inner and outer tubes. For the purposes of demonstrating separation of the conformers of the protein bovine ubiquitin all spectra were collected using P2 mode with DV=−3300 V. In addition to the high frequency waveform, a compensation voltage CV was also applied to the long inner cylinder 12. Although the CV can be scanned from −50 V to +50 V, the CV spectra herein are only shown from −12 V to 0V since the ions of bovine ubiquitin were transmitted through FAIMS within this CV window.

In this study, nitrogen gas was passed through a charcoal/molecular sieve gas purification cylinder and introduced into the FAIMS device through the carrier in ($C_{in}$) port at a flow rate of 6 L/min; The gas exited through the sample out ($S_{out}$) port at 1 L/min and through the carrier out ($C_{out}$) port at 5 L/min. The sample in ($S_{in}$) port was plugged in this study. A fraction of $C_{in}$ was directed radially inward through the 5 mm gap 11A between the inner cylinders 11, 12, and acted to help desolvate the ions. While the ions formed by ESI were driven radially outward through the gap by the electric field, the inward flow of curtain gas prevented neutrals from entering the annular analyzer region. This portion of $C_{in}$, along with the neutrals, exited the FAIMS device via the $S_{out}$ port.

The electrospray ions were carried by the gas stream along the length of the annular space between the outer cylinder and the long inner cylinder. If the combination of DV and CV was appropriate, and the ions were not lost to the tube walls, ions were transferred to the vacuum chamber of a mass spectrometer through the orifice 19 in the "sampler cone" 18 placed at the end of the FAIMS analyzer.

A custom interface was constructed for a tandem combination of FAIMS and a PE Sciex API 300 triple quadrupole mass spectrometer. The voltage of the sampler cone 18 was set to 44 V, whereas the skimmer cone 18A of the API 300 remained at ground potential for all experiments. The small ring electrode normally located behind the orifice of the conventional API 300 interface was not incorporated into the new interface, resulting in some loss of sensitivity. Behind the skimmer cone, in a low pressure region ($\sim 7 \times 10^{-3}$ torr), was an rf-only quadrupole (Q0) mass spectrometer 19A which acted to collisionally focus ions prior to their transmission into the first analyzer quadrupole (Q1). The voltage drop between the skimmer cone 18A and Q0 controlled the energy of the collisions in this region. The higher the voltage drop, the greater the extent of fragmentation. Unless otherwise stated, Q0=−1 V was used.

Ion-selected CV spectra (IS-CV spectra) were obtained by scanning the compensation voltage applied to the FAIMS, while monitoring a single m/z value. "Total ion current" CV spectra (TIC-CV spectra) show the sum of the signal for all detected ions in a given m/z range as CV was scanned. The mass spectrum collected at fixed values of DV and CV revealed the identity of any ions transmitted through the FAIMS under those conditions.

The ubiquitin ions described and used in this experiment behave as type C ions, as shown in FIG. 1. Analogous to the description of the behavior of positive type A ions, provided earlier, and referring back to FIGS. 1 and 2, a type C ion will travel further during the negative portion of the waveform ($d_1 < d_2$), and will migrate toward the upper plate.

As explained earlier, there are a total of four modes of operation for FAIMS. The waveform with negative DV (FIG. 4B) yields spectra of types P2 and N1, whereas the reversed polarity waveform yields P1 and N2 type spectra. In general, low mass ions (m/z is usually less than 300) are of type A (FIG. 1) and are detected in mode 1, while larger ions, including the positively charged ubiquitin ions studied here, are type C ions and are detected in mode 2 (i.e. mode P2).

Figure 14A:
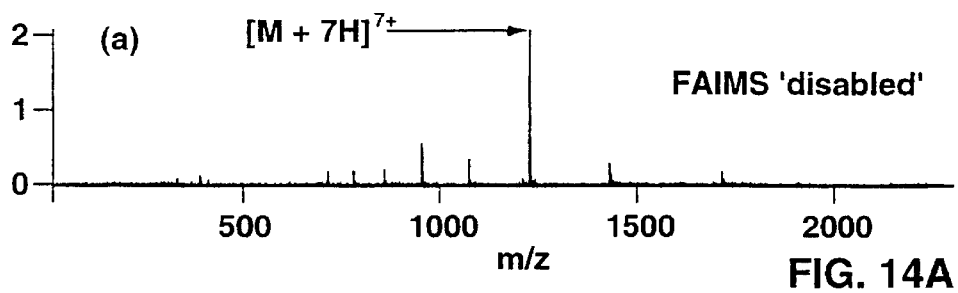
FIG. 14A shows an ESI mass spectrum for a solution of bovine ubiquitin.
Figure 14B:
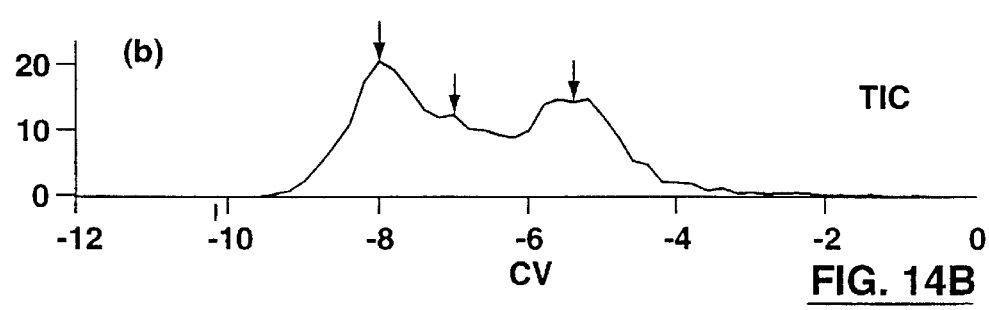
FIG. 14B shows a total ion current CV (TIC-CV) spectrum of a solution of bovine ubiquitin.
Figure 14C:
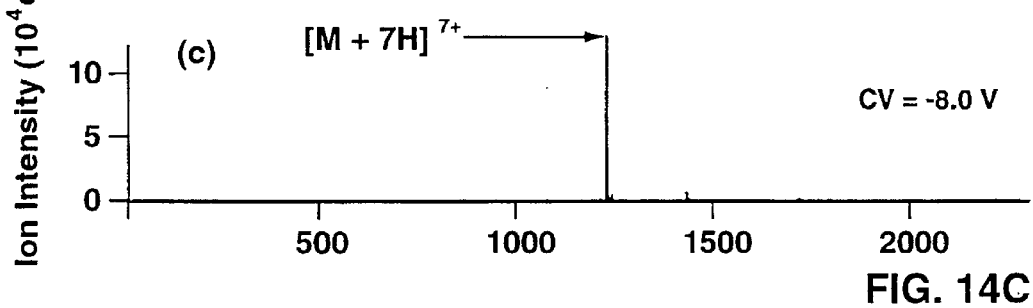
FIGS. 14C–14E show mass spectra obtained at several different CV values.
Figure 14D:
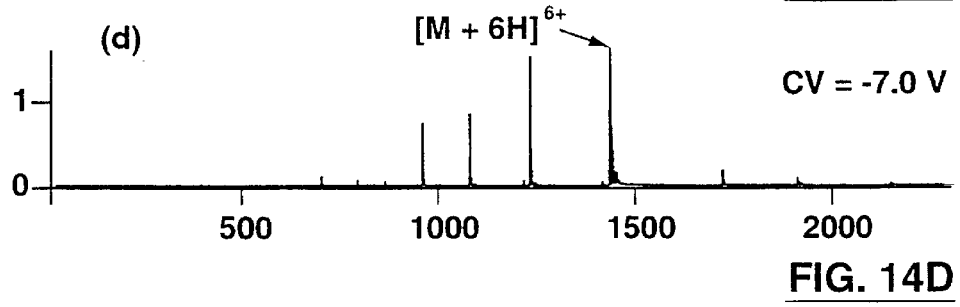
Figure 14E:
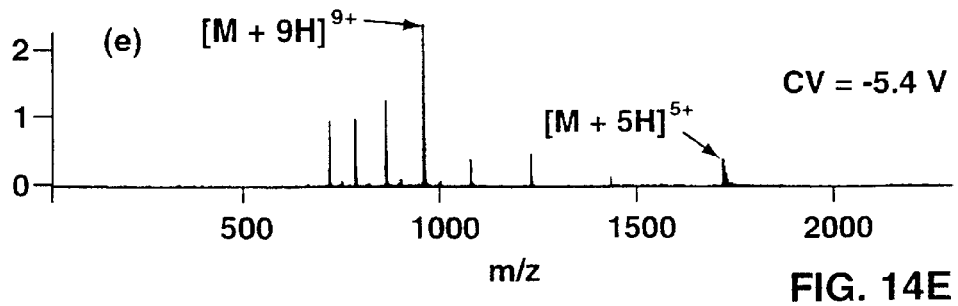

Now referring to FIG. 14A, an ESI-FAIMS-MS mass spectrum is shown for a solution of 5 $\mu$M bovine ubiquitin in 50/50/0.05 methanol/water/acetic acid (v/v/v) collected with FAIMS disabled. The solvent combination was selected for this illustration because several charge states are present. This mass spectrum essentially represents a conventional ESI-MS spectrum with somewhat lower sensitivity. FIGS. 14B–14E are ESI-FAIMS-MS spectra of the same solution used for FIG. 14A with FAIMS in operation (DV=−3300V): FIG. 14B shows a TIC-CV spectrum (m/z 30 to 2300), collected by scanning the CV from −12 V to 0 V, while FIGS. 14C–14E are mass spectra taken at specified CV values. The TIC-CV spectrum in FIG. 14B shows two distinct peaks with maxima at CV=−8.0 V and CV=−5.4 V. FIGS. 14C–14E illustrate ESI-FAIMS-MS mass spectra of protein ions, taken at CV values indicated by the arrows in FIG. 14B. The mass spectrum collected at CV=−8.0 volts (FIG. 14C) is dominated by the $[M+7H]^{7+}$ ion of bovine ubiquitin. Unlike the conventional ESI-MS spectrum, FIG. 14A, charge states higher than +7 are virtually absent in this mass spectrum. A mass spectrum (FIG. 14D) taken at the CV corresponding to the small shoulder off of the main peak, at CV=−7.0 V (FIG. 14B), shows a very different charge state distribution than FIG. 14C. The $[M+6H]^{6+}$ ion is the most abundant ion in this mass spectrum and several higher charge states are also observed. Finally, the mass spectrum at CV=−5.4 volts (FIG. 14E) shows yet another charge state distribution which is quite unlike the previous two mass spectra. In this spectrum, the $[M+7H]^{7+}$ ion is significantly reduced and the higher charge. states (along with charge state +5) have increased in intensity. The increase in sensitivity in the mass spectra collected with the FAIMS operating (FIGS. 14C–14E), compared with the mass spectra with the FAIMS disabled (FIG. 14A), is a result of the atmospheric pressure ion focusing mechanism discussed earlier.

The changes in the charge state distribution of the mass spectra collected at different CV values suggested that ion separation in FAIMS was sensitive to the structure of the protein ion. Consequently, IS-CV spectra for the individual charge states of bovine ubiquitin were collected using mass spectrometry, for the same solution as used to collect the data shown on FIG. 14A, for charge states +5 to +13.

Figure 15:
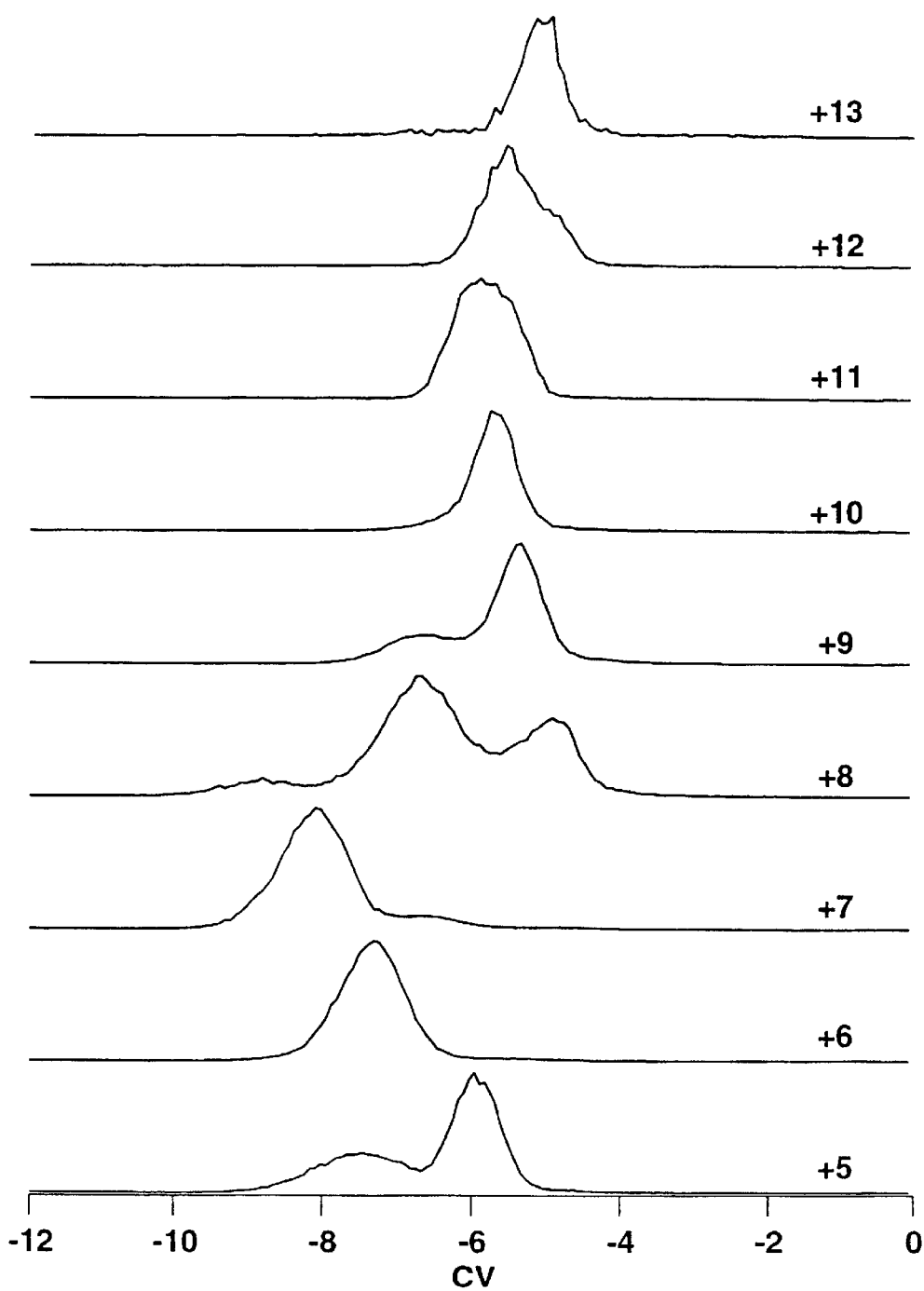
FIG. 15 shows normalized IS-CV spectra for various charge states of bovine ubiquitin ranging from +5 to +13 using the same solution as that used for FIG. 14.

Now referring to FIG. 15, some charge states (e.g., +10) show only one peak while others show multiple peaks (e.g., +8). Since the CV values for charge state +7 (m/z 1224.6) are more negative than the CV values for charge state +6 (m/z 1426.6) which are in turn more negative than the CV values for charge state +10 (m/z 857.5), the position of the peak in an IS-CV spectrum is clearly not a function of m/z. The multiple peaks which appear in several of the IS-CV spectra in FIG. 15 are attributed to coexisting, and distinct conformations of bovine ubiquitin. In the following discussion we will illustrate the behavior of several of the conformers of bovine ubiquitin, as a function of solution phase conditions including the solvent composition and the pH.

Effect of Acid

Different concentrations of acetic acid were used with 5 $\mu$M solutions (55:45 $H_2O$/MeOH v/v) of bovine ubiquitin to observe changes in the mass spectra and the CV spectra as a function of pH. The composition of the solvent has been selected to yield suitable mixtures of conformations for illustrating the effects of pH in the experiments discussed below. This solvent mixture was used for the data appearing in FIGS. 16 to 19. FIGS. 16A, 16C, and 16E, show mass spectra collected with the FAIMS disabled for 3 acetic acid (HOAc) concentrations from 0.04% to 4%, while FIGS. 16B, 16D, and 16F show the corresponding TIC-CV spectra (m/z from 30 to 2300) collected with the FAIMS in operation (DV=−3300V). At 0.04% acetic acid FIG. 16A, the higher charge states are present at very low abundances (with 60% $H_2O$ by volume these charge states are no longer observed). This spectrum is very similar to one reported in an earlier study for bovine ubiquitin is in its native state.

The TIC-CV spectrum in FIG. 16B for the 0.04% acetic acid solution shows a strong peak at CV=−8.2 V with a small shoulder at CV=−6.0 V. The mass spectrum (FAIMS disabled) collected using a solution containing 0.4% HOAc (FIG. 16C) shows a second charge state distribution, centered around $[M+12H]^{12+}$, in addition to the distribution centered at $[M+7H]^{7+}$. This second distribution is consistent with spectra collected for bovine ubiquitin in its denatured form as reported in an earlier study. The TIC-CV spectrum in FIG. 16D for the 0.4% HOAc solution has a second peak at CV=−5.8 V, presumably due to the presence of the denatured bovine ubiquitin. Finally, at 4% acetic acid, the low sensitivity ESI-MS spectrum (FIG. 16E) shows almost exclusively the higher charge states. The TIC-CV spectrum (FIG. 16F) shows essentially one peak located at CV=−6.0 V. Consequently, it is clear that the changes in the TIC-CV spectra collected with the FAIMS in operation (DV=−3300 V) reflect changes seen in the mass spectra of bovine ubiquitin with the FAIMS disabled.

FIGS. 17A–17I show IS-CV spectra for some of the charge states (i.e., +7, +8, and +9) of bovine ubiquitin as a function of pH. Traces were obtained using the same solutions as traces in FIGS. 16A–16F. The CV spectra of some of the charge states, such as +10 to +13, did not show significant changes as a function of pH and were excluded from the Figure.

Figure 17A:
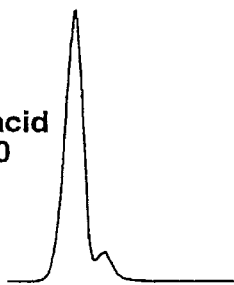
FIGS. 17A–17I show IS-CV spectra showing the effect of the amount of acetic acid in a solution of bovine ubiquitin on the charge states +7, +8 and +9.
Figure 17B:
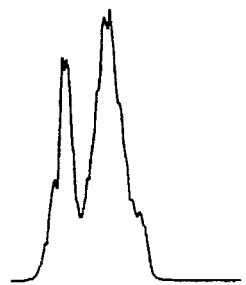
Figure 17C:
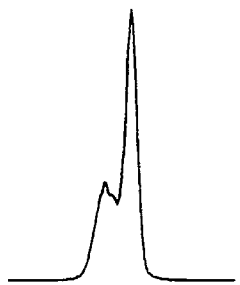
Figure 17D:
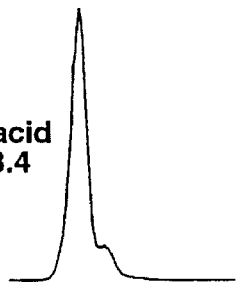
Figure 17E:
Figure 17F:
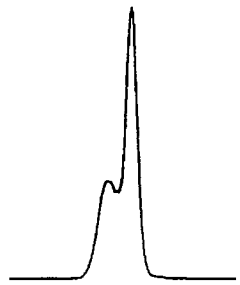
Figure 17G:
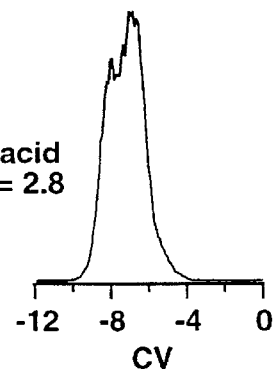
Figure 17H:
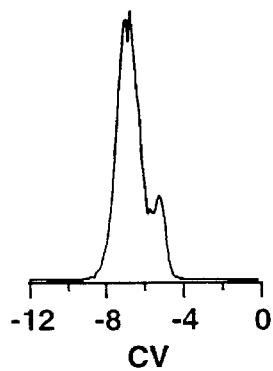
Figure 17I:
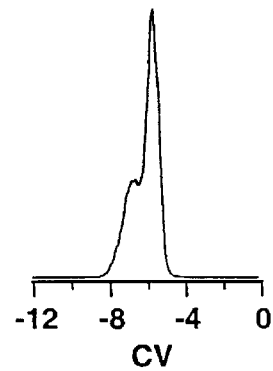

FIGS. 17A–17C are the IS-CV spectra of the +7, +8, and +9 charge states, respectively, collected using 0.04% acetic acid. These spectra reflect conditions in which the bovine ubiquitin is essentially in its native state. For charge state +8 in FIG. 17B, two main peaks are observed at CV~−9 V and ~−7 V. With 0.04% acetic acid, in the same solution, FIG. 17E, the IS-CV spectrum for charge state +8 changes significantly. The peak that is observed CV~−9V is now virtually absent from the spectrum and a new peak at CV~−5 V is visible. This change suggests that as the bovine ubiquitin begins to unfold the conformer of bovine ubiquitin, reflected by the peak at CV~−9 V, is no longer favorable. At a concentration of 4% acetic acid, FIG. 17H, the peak at ~−9 V is now completely absent from the spectrum. Charge state +7, FIGS. 17A, 17D, and 17G, also experiences significant changes with increasing concentrations of acetic acid. At low acetic acid levels, FIG. 17A, the IS-CV spectrum is dominated by a peak located at CV~−8 V. However, when 4% acetic acid is used, FIG. 17G, the IS-CV spectrum shows a shift that now favors the conformer which is present at CV~−7 V. FIGS. 17C, 17F, and 17I show that charge state +9 did not show significant changes as a function of pH.

To investigate behavior of the conformers at even lower pH values, hydrochloric acid, HCl, was added to solutions of 5 $\mu$M bovine ubiquitin (solutions were still 55% $H_2O$ by volume). IS-CV spectra at pH 2.8, 2.1, and 1.8 are shown in FIGS. 18A–18I. The top traces (FIGS. 18A, 18B, and 18C) were obtained at the same pH as the last experiment in FIGS. 17G, 17H, and 17I (i.e., pH ~2.8). This was done to permit a comparison based on changing the acids only. The IS-CV traces for charge states +8 and +9 at pH 2.8 (FIGS. 18B, and 18C) in HCl are very similar to that observed in FIGS. 17H, and 17I using acetic acid at pH 2.8. The IS-CV spectra for the other charge states not shown also gave similar results. However, the IS-CV spectrum for charge state +7 in HCl at pH 2.8 (FIG. 18A) shows significant differences from the IS-CV spectrum (FIG. 17G) for charge state +7 at pH 2.8 in acetic acid. The former spectrum more closely resembles IS-CV spectra for acetic acid at slightly higher pH values, but with an additional peak at CV~−5 V that was not observed when using acetic acid.

By decreasing the pH from 2.8 (FIGS. 18A, 18B, and 18C) to 2.1 in FIGS. 18D, 18E, and 18F, there are significant changes that are observed for charge states +7, +8, and +9 respectively (and others). In all instances, a peak at a CV of between −5 and −6 V becomes favored. This trend is continued as the pH is lowered even further to 1.8 (FIGS. 18G, 18H, and 18I). The IS-CV spectra that were obtained for this solution were markedly more noisy and less intense. However, the dominance of the peak at the least negative CV value is still apparent.

Figure 19:
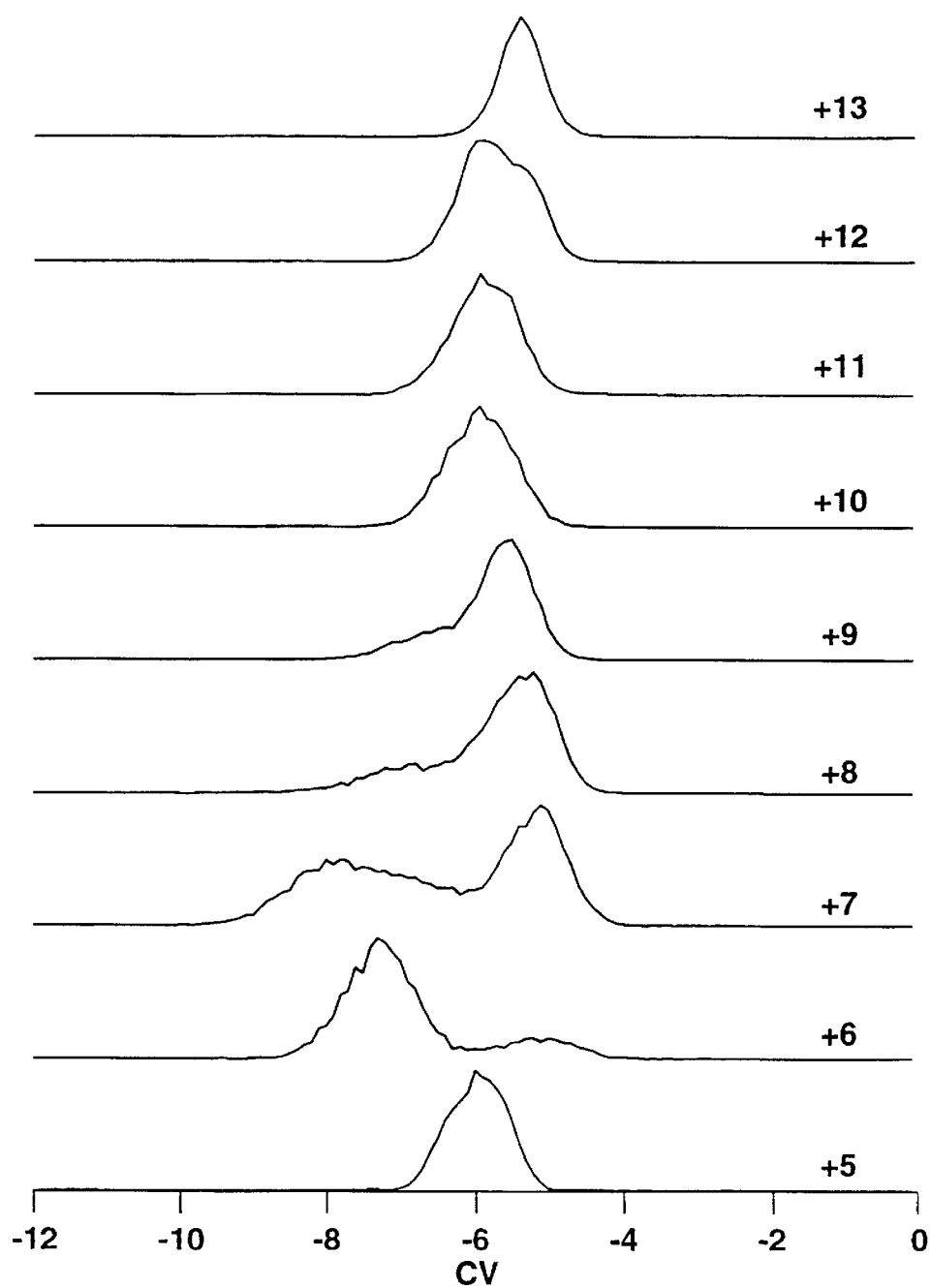
FIG. 19 shows normalized IS-CV spectra for the charge states +5 to +13 using a 5 $\mu$M solution of bovine ubiquitin (55% water) acidified to pH 2.1 using HCl.

The data illustrated in FIGS. 15 and 19 permit a comparison of the CV spectra of bovine ubiquitin at several charge states, using solutions of acetic acid at pH 3.4 (FIG. 15, 50:50 water/MeOH) with CV spectra collected using a solution acidified to pH 2.1 with HCl (FIG. 19, 55:45 water/MeOH). The traces for charge states +10 through +13, in FIG. 19, are very similar to those observed in FIG. 15. Changes in the CV spectra of charge states +5 through +9 were observed.

Effect of Solvent

Figure 20A:
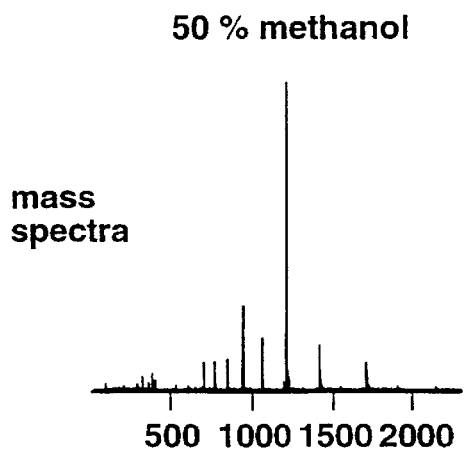
FIGS. 20A–20F show the effect of solvent composition on mass spectra, TIC-CV spectra, and IS-CV spectra of bovine ubiquitin.
Figure 20B:
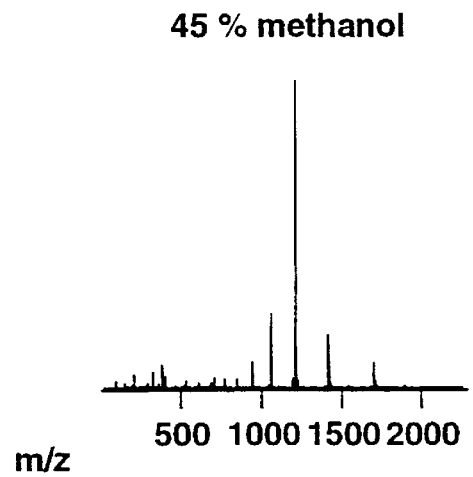
Figure 20C:
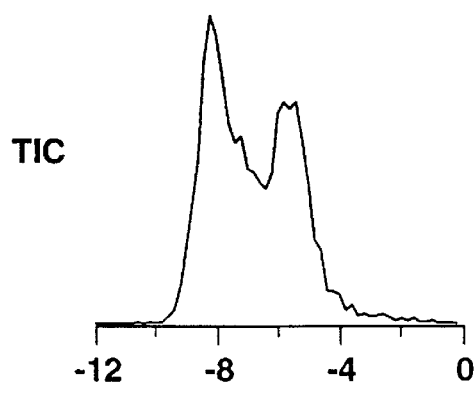
Figure 20D:
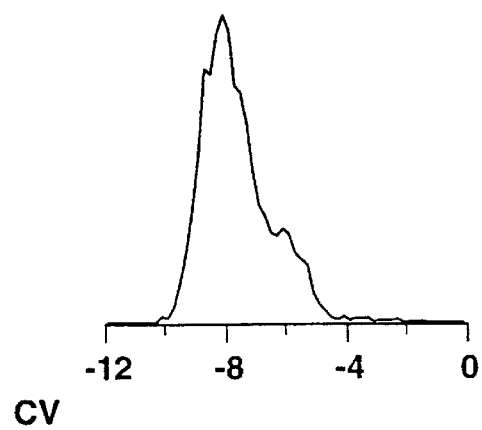
Figure 20E:
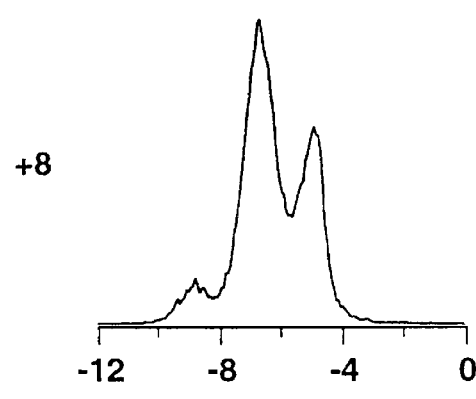
Figure 20F:
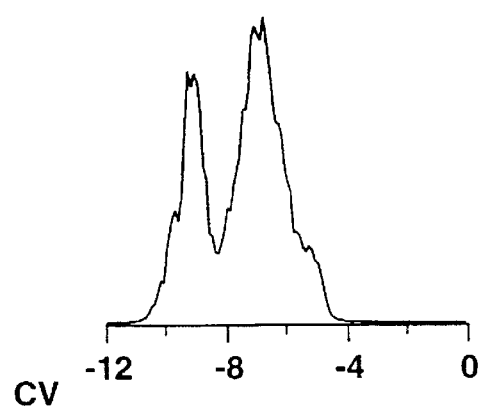

The CV spectra and mass spectra shown in FIG. 20 illustrate the effect of changing the solvent mixture from 50:50 water/MeOH FIGS. 20A, 20C, and 20E, to 55:45 water/MeOH v/v FIGS. 20B, 20D, and 20F, while maintaining low acid (0.04% HOAc) concentration. The mass spectra (FIGS. 20A and 20B) were collected with the FAIMS disabled while the CV spectra (FIGS. 20C through 20F) were collected with the FAIMS in operation (DV=−3300V). As is consistent with previous studies, increasing amounts of organic solvent cause bovine ubiquitin to denature. This is shown by the slight increase in the higher charge states of mass spectra acquired with the solution containing the higher percentage of organic solvent (FIG. 20A, 50% MeOH) relative to that shown for lower percent organic solvent (FIG. 20B). The FAIMS CV spectra also reflect this change in solvent composition as indicated in the TIC-CV spectra in FIGS. 20C and 20D. Furthermore, the IS-CV spectrum for charge state +8 (FIGS. 20E, and 20F) also undergoes a significant change over this solvent range. The peak at −9 V in the CV spectrum of the +8 charge state collected using a solution containing 50% MeOH (FIG. 20E) is much less intense than that observed at −9 V for a solution which contained 45% MeOH (FIG. 20F).

Exchange Reactions

Mass spectra of the three distinct peaks observed in the CV spectrum of charge state +8 (FIG. 21A) were collected to investigate differences among the conformers of this charge state. The CV spectrum (FIG. 21A) and the mass spectrum collected for each peak, for a solution containing 5 $\mu$M bovine ubiquitin in 50% $H_2O$ and 0.04% acetic acid are shown in FIGS. 21C, 21E, and 21G. The expanded views of the mass spectra show that several sodium ions have replaced protons, $(M+nH+mNa)^{+n+m}$ where n+m=8, in each conformation of the +8 charge state of bovine ubiquitin. The mass spectrum of the peak at CV=−4.8 V (FIG. 21G) clearly shows up to four sodium replacements, the mass spectrum of the peak at CV=−8.9 V (FIG. 21C) shows virtually no proton replacement, and the mass spectrum of the peak at CV=−6.9 volts (FIG. 21E) shows that up to two sodium ions have replaced protons in the +8 ion. We speculate that the differences in the aqueous phase, three-dimensional structures of the conformers of the +8 charge state of the bovine ubiquitin ion have resulted in varying degrees of replacement of protons by sodium ions in the gas-phase conformer.

It could be argued that the location of these adducts in the CV spectrum is not a consequence of the different conformations of bovine ubiquitin, but instead that the sodium adduct actually causes the ions to be located in the CV spectrum as shown in FIG. 21A. Previous results with ESI-FAIMS-MS obtained by the inventors have shown that for a smaller species (e.g., leucine enkephalin, MW 555.5), adduct ions can alter the CV of a given species in the compensation voltage spectrum. Consequently, two additional experimental results are described to show that the presence of different degrees of sodium replacement is a result of the different conformations, and that the location of the ion in these CV spectra is not altered by replacement of protons with sodium ions.

The spectra in FIGS. 21B, 21D, 21F, and 21H were obtained after 1mM of sodium chloride was added to the solution that was used to collect the data for FIGS. 21A, 21C, 21E, and 21G. Note that due to the distribution of the sodium-containing ions over several m/z values, the IS-CV spectrum collected in FIG. 21B was collected over the m/z range 1071–1080 rather than at m/z 1071.6 exclusively. The IS-CV spectra in FIGS. 21A and 21B are very similar, and the CV values of the three peaks corresponding to +8 of bovine ubiquitin have not changed significantly. However, the expanded views of the mass spectra collected for these three species have changed. Furthermore, the mass spectrum for the species at CV=−4.8 V with no sodium added (FIG. 21G) is very similar to the mass spectra for the species at CV=−6.9 V with 1 mM sodium added (FIG. 21F). The question to be asked is whether the number of sodium ions bound to the protein ion determine its position in the CV spectrum or does the conformation of the protein ion determine the degree of sodium substitution. If the replacement of protons with sodium ions was causing the CV shift, these two mass spectra should be observed at virtually identical locations in the CV spectra. Thus, the number of sodium replacements reflects structural differences in the conformers represented by the three peaks observed for the +8 state of bovine ubiquitin.

Figure 22A:
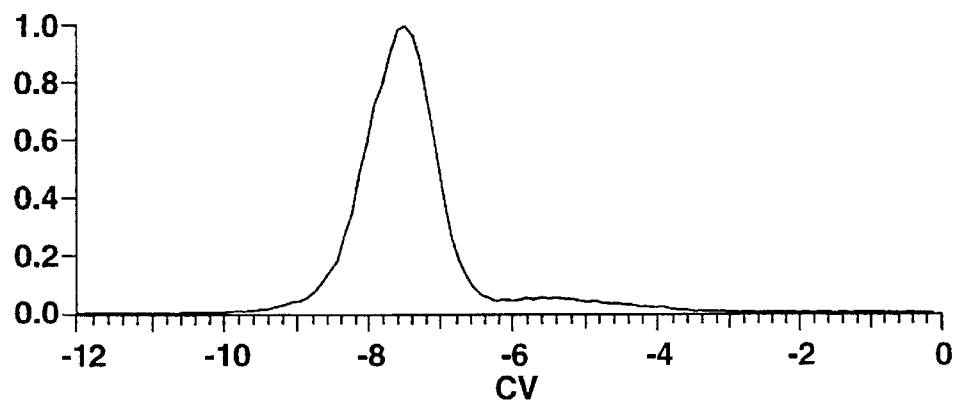
FIG. 22A shows an IS-CV spectrum showing the dependence of sodium adduct ion intensity on the conformation for the +6 charge state of bovine ubiquitin.
Figure 22B:
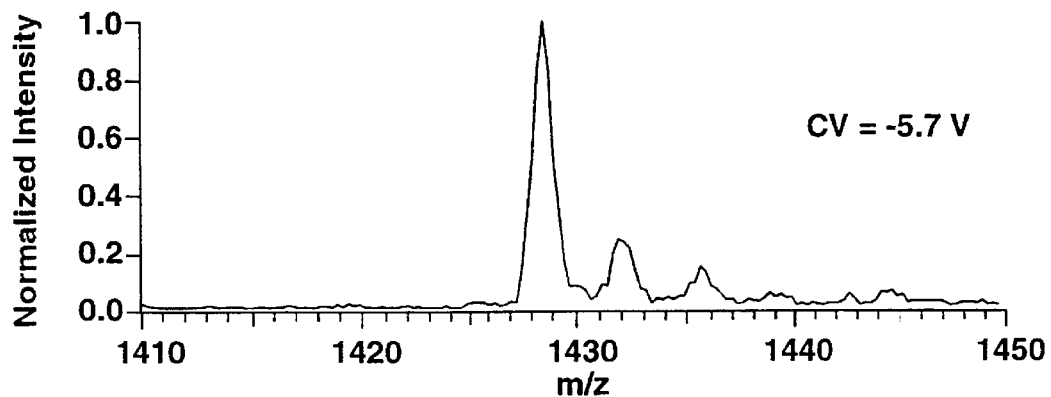
FIGS. 22B and 22C show mass spectra for the solution used in FIG. 21A at two different CV values.
Figure 22C:
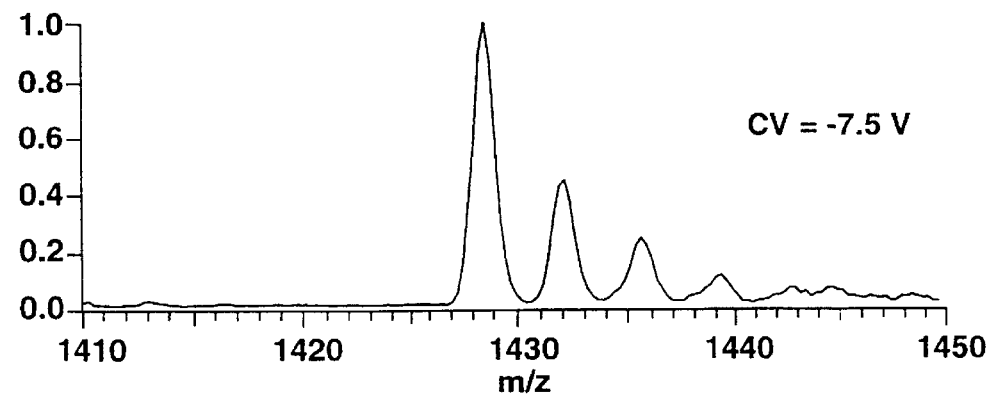

An IS-CV spectrum for the +6 charge state (FIG. 22A) is dominated by a peak at CV=−7.5 V, however there is also a smaller peak at CV=−5.7 V. FIGS. 22B and 22C show mass spectra that were collected for these peaks at CV=−5.7 V and CV=−7.5 V (note FIG. 22B represents a sum of 50 mass spectra). For this charge state, the ion which is amenable to higher level of sodium replacement of protons is observed at the more negative CV of the two conformers. Conversely, the data for the +8 charge state of bovine ubiquitin (FIG. 21), indicates that the conformer which accumulates the higher number of sodium ions was observed at less negative CV values.

Figure 23A:
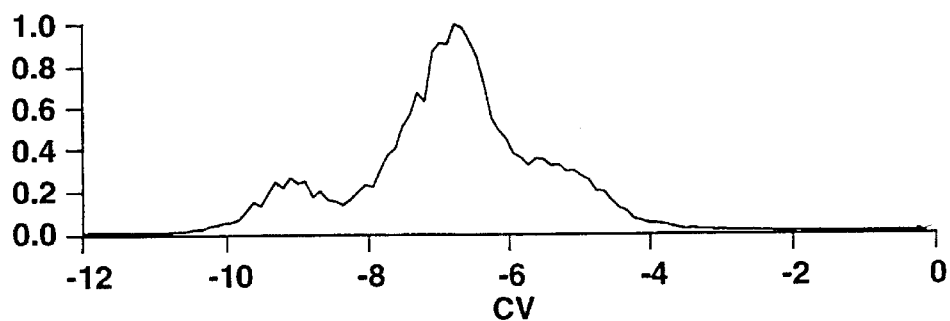
FIG. 23A shows an IS-CV spectrum for the +8 charge state of bovine ubiquitin using a solution containing phosphate.
Figure 23B:
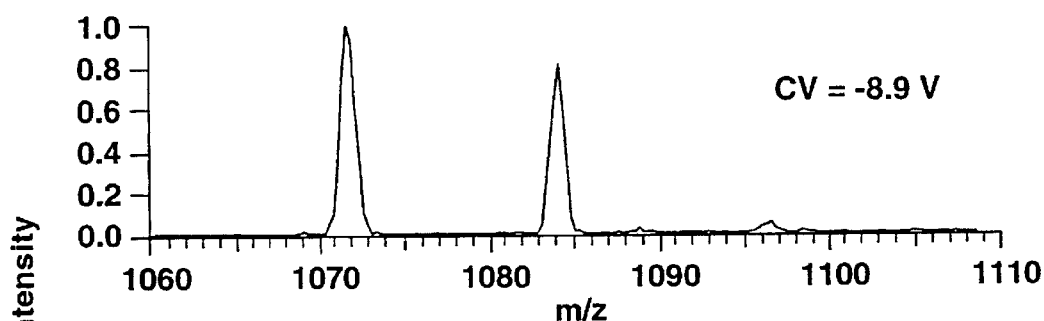
FIGS. 23B–23D show mass spectra for the solution used in FIG. 23A at three different CV values.
Figure 23C:
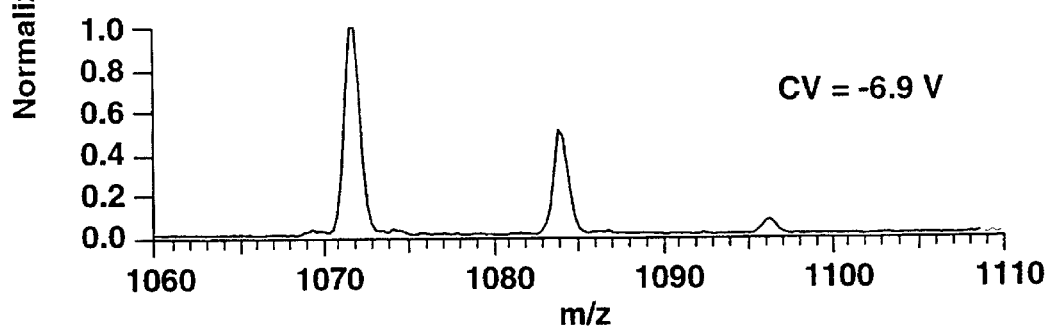
Figure 23D:
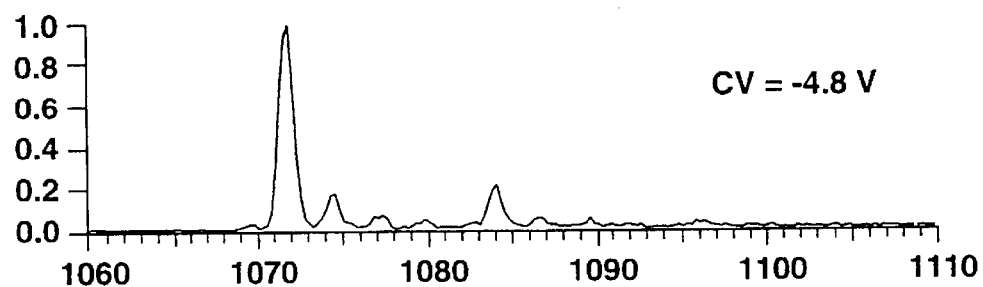

The effect of other species, beside sodium, on CV spectra for bovine ubiquitin was also investigated. FIG. 23 shows ESI-FAIMS-MS data collected using an excess of potassium di-hydrogen phosphate added to a solution of 5 $\mu$M bovine ubiquitin in 50% $H_2O$ and 0.02% acetic acid. FIG. 23A shows an IS-CV spectrum for the +8 charge state of bovine ubiquitin that is very similar to that observed previously in this study for solutions of 50% $H_2O$, FIG. 21A. The change in the relative abundances of the conformers at CV~−9 V and ~−5 V compared with, for example, FIG. 21A, can be attributed to the change in pH caused by the difference in HOAc concentration, and added $KH_2PO_4$. Expanded views of the mass spectra, obtained at CV values −8.9 V, −6.9 V, and −4.8 V in FIG. 23A, are shown in FIGS. 23B, 23C, and 23D, respectively, and show significant differences in the abundances of phosphate adducts. As was observed with sodium, the degree of adduct formation is a function of the conformer. However, the results in FIG. 23 show the opposite trend compared with the results shown in FIG. 21. That is, in FIG. 23, the conformer that appears in the CV spectrum at CV~−9 V (FIG. 23B) shows the most intense phosphate adduct ion whereas the conformer that appears in the CV spectrum at CV~−5 V shows the least intense phosphate ion adduct (FIG. 23D). Note also that the addition of phosphate did not modify the CV at which each of the three conformers appeared (compare to FIG. 21A). We also note that none of the three conformers of the +8 ion had a tendency to replace protons with potassium ions.

These examples illustrate that by examining 'spectator' ions such as sodium and phosphate, we can gain clues into the differences in the individual conformations. Experiments have indicated that the replacement/addition of the 'spectator' has not affected the ion conformation. It is possible that the formation of some replacements/additions may lead to significant changes in the conformation of an ion. Such a change would be expected (in most cases) to be reflected by peak shifts in the IS-CV spectra.

Concentration Effects

In an earlier study, the inventors observed more than one peak in an IS-CV spectrum of a solution of leucine enkephalin (m/z 556.5) with ESI-FAIMS-MS (see R. Purves and R. Guevremont, Anal. Chem. 71, 2346 (1999), R. Guevremont and R. Purves J. Am. Soc. Mass Spectrom. 10, 492 (1999)), and attributed the additional peaks to a series of cluster ions of the type $(nM+nH)^{n+}$. To ensure that the different peaks observed in the IS-CV spectra in this study (e.g. FIG. 15) were not a consequence of the formation of multimers or other cluster ions, different concentrations of bovine ubiquitin were studied. For the concentration range from 1 $\mu$M to 100 $\mu$M bovine ubiquitin (in 50% water and 0.04% acetic acid), no significant changes in the shapes of the IS-CV spectra for any charge state were observed. If the multiple peaks in an IS-CV spectrum were caused by the formation of cluster ions, the relative amounts of the various peaks in an IS-CV spectrum would change as a function of concentration.

Comparison with Drift Tube Mobility Spectrometry

ESI-drift tube mobility spectrometry/MS has been used to examine the conformations of a number of proteins. The separation of conformers in a drift tube is based on the ion cross section, whereas the separation of ions in FAIMS is based on heretofore unknown properties of the ions. It is expected therefore, that there will be many similarities, and also significant differences in the array of conformations detected by these two, independent approaches.

Figure 24:
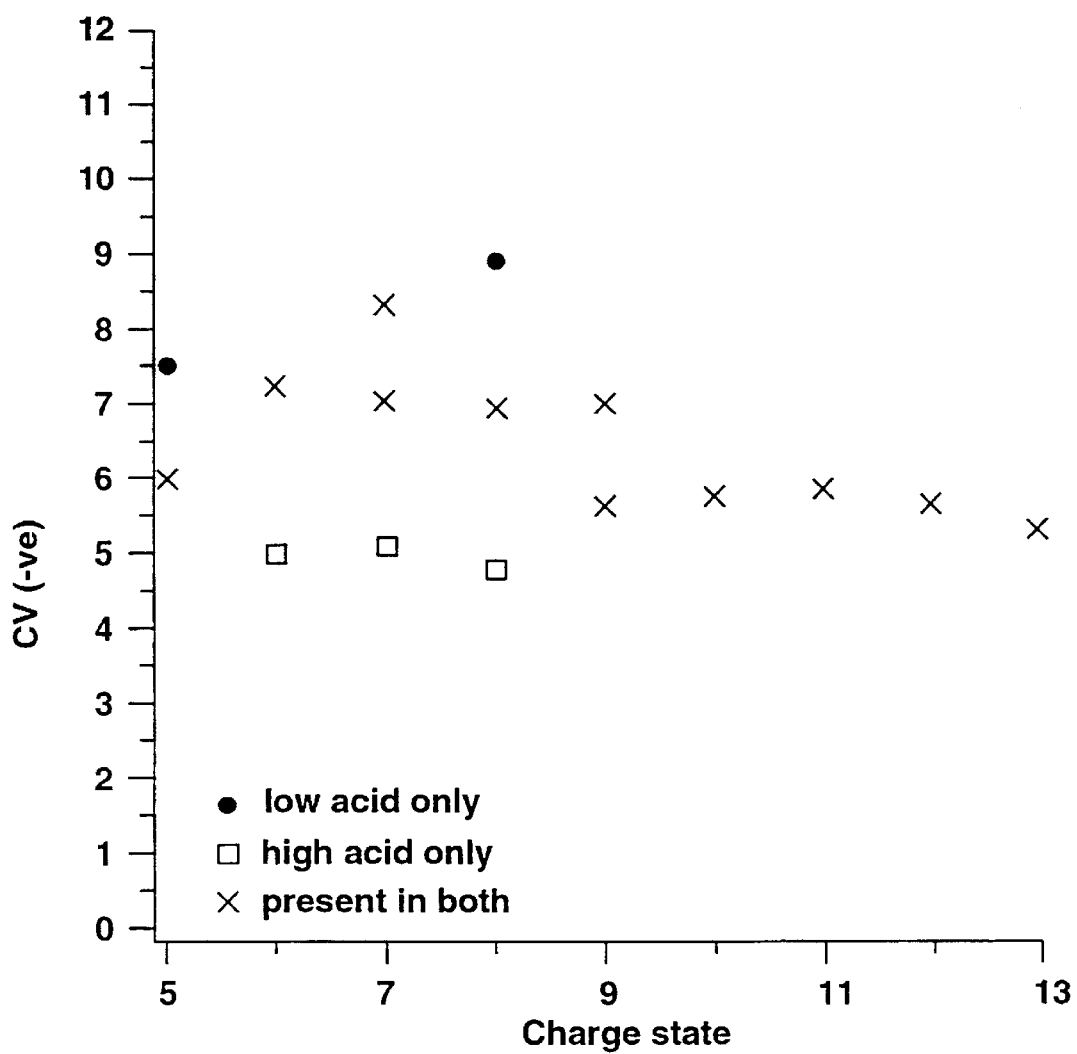
FIG. 24 is a plot showing the location of the peak maxima for all conformers of bovine ubiquitin observed in this study.

Valentine et. al. have used their ESI-drift tube mobility spectrometry/MS, and proton transfer reagents, to study the conformers of bovine ubiquitin (S. J. Valentine, A. E. Counterman, D. E. Clemmer, J. Am. Soc. Mass Spectrom. 8, 954 (1997)). In their work, the authors divided their results for collision cross section into three types of conformations: elongated, partially folded, and compact. FIG. 24 summarizes the conformational information obtained for bovine ubiquitin by ESI-FAIMS-MS as a plot of CV values for each of the peaks appearing in the CV spectra for each of the individual charge states. The "low acid" solution contained 55% $H_2O$ and 0.04% acetic acid while the "high acid" solution contained 55% $H_2O$ and the pH adjusted to 2.1 with HCl. The peak maxima that were observed in the IS-CV spectra were classified as being observed either in the "low acid" solution, the "high acid" solution, or both.

For some charge states in FIG. 24 (i.e., +10 through +13), the CV remains approximately constant between −5 and −6 V independent of the acid concentration (pH). For the remaining charge states (i.e., +5 through +9), there are several resolved conformers, and the relative abundances of the conformers is dependent on the solution conditions. The most negative CV values are observed for conformers only present in the "low acid" solution. For charge states +5 through +8, Valentine et. al. reported the co-existence of elongated and partially folded conformations. Consequently, both FAIMS, and drift tube mobility spectrometry techniques identified the same charge states having a multiplicity of conformations.

Although the invention has been described and illustrated with reference to specific embodiments, those skilled in the art will recognize that the invention may be otherwise embodied within the scope of the following claims. Specifically, while the experiments describe the use of a mass spectrometer to measure transmitted ions at an ion outlet of a FAIMS device, it will be understood that a mass spectrometer is not necessary once the values for DV, CV and other operating conditions for the FAIMS device have been determined for separating a desired ion. Thus, collection of desired transmitted ions may occur at the ion outlet of a FAIMS device, rather than entering a mass spectrometer for measurement.

We claim:

1. A method for identifying ions having substantially the same mass to charge ratio but having different ion mobility characteristics, comprising the steps of:
   a) providing at least one ionization source of ions;
   b) providing an analyzer region defined by a space between at least first and second spaced apart electrodes, said analyzer region being in communication with a gas inlet, a gas outlet, an ion inlet and an ion outlet, and introducing said ions into said analyzer region through said ion inlet;
   c) applying an asymmetric waveform voltage and a direct current compensation voltage to at least one of said electrodes;
   d) setting said asymmetric waveform voltage;
   e) varying said direct current compensation voltage and measuring resulting transmitted ions at said ion outlet, so as to produce a compensation voltage scan for said transmitted ions; and
   f) identifying peaks in said compensation voltage scan.

2. The method claimed in claim 1, further comprising the step of setting said direct current compensation voltage to correspond to one of said peaks to separate a desired ion from other ions with substantially the same mass to charge ratio.

3. The method claimed in claim 2, which includes operating substantially at atmospheric pressure and substantially at room temperature.

4. The method claimed in claim 2, which includes generating said ions for said source of ions by electrospray ionization.

5. The method claimed in claim 2, which includes detecting said transmitted ions by mass spectrometry.

6. The method claimed in claim 5, which includes subjecting the transmitted ions to a mass analysis scan to provide ion intensity data over a selected range of mass to charge ratios.

7. The method claimed in claim 2, which includes providing a gas flow through said analyzer region, so as to transport said ions along said analyzer region.

8. The method as claimed in claim 2, which includes collecting the desired ions for further processing.

9. The method claimed in claim 1, which includes generating ions from isomers as said source of ions.

10. The method claimed in claim 9, which further includes selecting said isomers from the group comprising stereoisomers, enantiomers, diastereomers, constitutional isomers, geometrical isomers, positional isomers, and cis-trans isomers.

11. The method claimed in claim 9, wherein, said isomers are leucine and isoleucine.

12. The method claimed in claim 1, which includes generating ions from conformers as said source of ions.

13. The method claimed in claim 12, which further includes selecting said conformers from one of synthetic polymers and biological polymers.

14. The method claimed in claim 13, wherein, said conformers are different conformers of bovine ubiquitin.

15. A method for identifying constitutional isomers, comprising the steps of:
   a) providing at least one ionization source of at least one constitutional isomer;
   b) providing an analyzer region defined by a space between at least first and second spaced apart electrodes, said analyzer region being in communication with a gas inlet, a gas outlet, an ion inlet and an ion outlet, and introducing said ions into said analyzer region through said ion inlet;
   c) applying an asymmetric waveform voltage and a direct current compensation voltage to at least one of said electrodes;
   d) setting said asymmetric waveform voltage;
   e) varying said direct current compensation voltage and measuring resulting transmitted ions at said ion outlet, so as to produce a compensation voltage scan for said transmitted ions; and
   f) identifying peaks in said compensation voltage scan corresponding to a constitutional isomer.

16. The method claimed in claim 15, further comprising the step of setting said direct current compensation voltage to correspond to a peak so as to separate a desired constitutional isomer.

17. The method as claimed in claim 16, which includes collecting the desired constitutional isomers for further processing.

18. The method claimed in claim 15, which includes operating substantially at atmospheric pressure and substantially at room temperature.

19. The method claimed in claim 15, which includes detecting said transmitted ions by mass spectrometry.

20. The method claimed in claim 15, which includes providing a gas flow through said analyzer region, so as to transport said ions along said analyzer region.

21. A method for separating one of leucine ions and isoleucine ions from a gaseous mixture of leucine and isoleucine ions, comprising the steps of:
   a) providing a solution of leucine and isoleucine;
   b) producing a gaseous mixture of leucine and isoleucine ions from said solution of leucine and isoleucine ions;
   c) providing an analyzer region defined by a space between at least first and second spaced apart electrodes, said analyzer region being in communication with a gas inlet, a gas outlet, an ion inlet and an ion outlet, and introducing said leucine and isoleucine ions into said analyzer region through said ion inlet;
   d) applying an asymmetric waveform voltage and a direct current compensation voltage to at least one of said electrodes;
   e) setting said asymmetric waveform voltage; and
   f) setting said direct current compensation voltage to separate one of said leucine and isoleucine ions from said ion mixture.

22. The method claimed in claim 21, which includes operating substantially at atmospheric pressure and substantially at room temperature.

23. The method claimed in claim 21, which includes providing a gas flow through said analyzer region, so as to transport said ions along said analyzer region.

24. The method claimed in claim 21, which includes generating negatively charged leucine and isoleucine ions.

25. A method for identifying different conformers, comprising the steps of:
   a) providing at least one ionization source for producing a sample of different conformers;
   b) providing an analyzer region defined by a space between at least first and second spaced apart electrodes, said analyzer region being in communication with a gas inlet, a gas outlet, an ion inlet and an ion outlet, and introducing said sample into said analyzer region through said ion inlet;
   c) applying an asymmetric waveform voltage and a direct current compensation voltage to at least one of said electrodes;
   d) setting said asymmetric waveform voltage;
   e) varying said direct current compensation voltage and measuring resulting transmitted ions at said ion outlet, so as to produce a compensation voltage scan of said transmitted ions; and
   f) identifying peaks in said compensation voltage scan corresponding to different conformers.

26. The method claimed in claim 25, further comprising the step of setting said direct current compensation voltage to substantially correspond to a peak so as to separate a desired conformer.

27. The method claimed in claim 25, wherein, said analyzer region is operated substantially at atmospheric pressure and substantially at room temperature.

28. The method claimed in claim 25, wherein, said sample is produced by electrospray ionization.

29. The method claimed in claim 25, which includes detecting said transmitted ions by mass spectrometry.

30. The method claimed in claim 29, which includes subjecting the transmitted ions to a mass analysis scan to provide ion intensity data over a selected range of mass to charge ratios, so as to identify different conformations of ions at given charge states.

31. The method claimed in claim 25, which includes providing a gas flow through said analyzer region, so as to transport said ions along said analyzer region.

32. The method claimed in claim 25, wherein, said ions are conformers of bovine ubiquitin.

33. A method for identifying and/or separating one isomer from a mixture including two isomers, comprising the steps of:
   a) providing at least one ionization source for producing ions including two isomers;
   b) providing an analyzer region defined by a space between at least a first and second spaced apart electrodes, said analyzer region being in communication with at least one of each of a gas inlet, a gas outlet, an ion inlet and an ion outlet, and introducing said ions into said analyzer region through said ion inlet;
   c) applying an asymmetric waveform voltage and a direct current compensation voltage to at least one of said electrodes;
   d) setting said asymmetric waveform voltage in order to effect a difference in net displacement between said two isomers in the time of one cycle of said applied asymmetric waveform voltage;
   e) varying said direct current compensation voltage to compensate for some of the displacement of one of said two isomers, said displacement resulting from the applied asymmetric waveform voltage, and measuring resulting transmitted ions at said ion outlet, so as to produce a compensation voltage scan for said transmitted ions; and, f) identifying at least one peak in said compensation voltage scan corresponding to only one of said two isomers.

34. The method claimed in claim 33, further comprising the step of setting said direct current compensation voltage to correspond to one of said peaks to separate one of said two isomers.

35. The method claimed in claim 34, wherein said ions introduced into said ion inlet are produced by electrospray ionization.

36. The method claimed in claim 35, which includes detecting said transmitted ions by mass spectrometry.

37. The method claimed in claim 34, which includes detecting said transmitted ions by mass spectrometry.

38. The method claimed in claim 34, which includes collecting said one of said two isomers for further processing.

39. The method claimed in claim 34, which includes operating substantially at atmospheric pressure and substantially at room temperature.

40. The method claimed in claim 39, which includes collecting said one of said two isomers for further processing.

41. The method claimed in claim 33, which includes detecting said transmitted ions by mass spectrometry.

42. The method claimed in claim 41, which includes subjecting the transmitted ions into a mass analysis scan to provide ion intensity data over a selected range of mass to charge ratios.

43. The method claimed in claim 33, which includes providing a gas flow through said analyzer region, so as to transport said ions along said analyzer region.

44. The method claimed in claim 33, wherein step a) comprises providing ions including a pair of isomers selected from the group comprising stereoisomers, enantiomers, diastereomers, geometrical isomers, positional isomers, and cis-trans isomers.

45. The method claimed in claim 33, wherein step a) comprises providing ions generated from two constitutional isomers.

46. The method claimed in claim 33, wherein step a) comprises providing the isomers of leucine and isoleucine.

47. A method for identifying and/or separating different conformers, comprising the steps of:

a) providing at least one ionization source for producing a sample including different conformer ions of a same compound;

b) providing an analyzer region defined by a space between at least a first and second spaced apart electrodes, said analyzer region being in communication with at least one of each of a gas inlet, a gas outlet, an ion inlet and an ion outlet, and introducing said ions into said analyzer region through said ion inlet;

c) applying an asymmetric waveform voltage and a direct current compensation voltage to at least one of said electrodes;

d) setting said asymmetric waveform voltage in order to effect a difference in net displacement between said different conformer ions of a same compound in the time of one cycle of said applied asymmetric waveform voltage;

e) varying said direct current compensation voltage to compensate for some of the displacement of one of said two conformer ions, said displacement resulting from the applied asymmetric waveform voltage, and measuring resulting transmitted ions at said ion outlet, so as to produce a compensation voltage scan for said transmitted ions; and, f) identifying at least one peak in said compensation voltage scan corresponding to only one of said different conformer ions.

48. The method claimed in claim 47, further comprising the step of setting said direct current compensation voltage to correspond to one of said peaks to separate one of said different conformer ions.

49. The method claimed in claim 48, which includes operating substantially at atmospheric pressure and substantially at room temperature.

50. The method claimed in claim 48, wherein said ions introduced into said ion inlet are produced by electrospray ionization.

51. The method claimed in claim 50, which includes detecting said transmitted ions by mass spectrometry.

52. The method claimed in claim 51, which includes subjecting said transmitted ions into a mass analysis scan to provide ion intensity data over a selected range of mass to charge ratios.

53. The method claimed in claim 48, which includes detecting said transmitted ions by mass spectrometry.

54. The method claimed in claim 53, which includes subjecting said transmitted ions into a mass analysis scan to provide ion intensity data over a selected range of mass to charge ratios.

55. The method claimed in claim 48, which includes providing a gas flow through said analyzer region, so as to transport said ions along said analyzer region.

56. The method claimed in claim 48, wherein said ions are conformers of bovine ubiquitin.

57. The method claimed in claim 47, wherein step a) comprises providing ions generated from conformers which are one of synthetic polymers and biological polymers.

* * * * *